United States Patent
Gueiros-Filho et al.

(10) Patent No.: US 6,410,250 B1
(45) Date of Patent: *Jun. 25, 2002

(54) SUSTAINED DELIVERY DEVICE AND METHODS OF MAKING AND USING THE SAME

(75) Inventors: Frederico J. Gueiros-Filho, Boston; Stephen M. Beverley, Jamaica Plain; Dennis E. Vaccaro, Wellesley, all of MA (US)

(73) Assignee: Symbiontics, Inc., Wellesley, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/451,245

(22) Filed: Nov. 29, 1999

Related U.S. Application Data

(63) Continuation of application No. 08/735,507, filed on Oct. 23, 1996, now Pat. No. 6,020,144.
(60) Provisional application No. 60/026,006, filed on Sep. 12, 1996.

(51) Int. Cl.$^7$ ................ G01N 33/53; G01N 33/569; C12N 15/63; A61K 39/002; C07H 21/02

(52) U.S. Cl. ............... 435/7.22; 435/455; 424/269.1; 536/23.1; 536/23.2

(58) Field of Search ................ 536/23.1, 23.2; 424/93.1, 94.3, 269.1; 435/722, 455, 258.1, 258.3; 514/44

(56) References Cited

U.S. PATENT DOCUMENTS

| | | |
|---|---|---|
| 4,632,830 A | 12/1986 | Formal et al. |
| 4,735,901 A | 4/1988 | Kurtz et al. |
| 4,764,370 A | 8/1988 | Fields et al. |
| 5,229,112 A | 7/1993 | Obukowicz et al. |
| 5,294,441 A | 3/1994 | Curtiss, III |
| 5,387,744 A | 2/1995 | Curtiss, III et al. |
| 5,389,368 A | 2/1995 | Gurtiss, III |
| 6,020,144 A * | 2/2000 | Gueiros-Falho et al. ... 435/7.22 |

FOREIGN PATENT DOCUMENTS

| | | |
|---|---|---|
| EP | 0 249 449 A1 | 12/1987 |
| EP | 0 806 476 A2 | 11/1997 |
| WO | WO 91/18092 | 11/1991 |
| WO | WO 94/02591 | 2/1994 |
| WO | WO 95/06729 | 3/1995 |
| WO | WO 95/29239 | 11/1995 |
| WO | WO 96/06941 | 3/1996 |
| WO | WO 96/40238 | 12/1996 |

OTHER PUBLICATIONS

Linda Gritz et al., (1983) "Plasmid–encoded hygromycin B resistance: the sequence of hygromycin B phosphotransferase gene and its expression in *Escherichia coli* and *Saccharomyces cerevisiae*" vol. 25, *Gene*, pp. 179–188.

Charles E. Garrett et al., (1984) "A Bifunctional Thymidylate Synthetase–Dihydrofolate Reductase in Protozoa" vol. 11, *Molecular and Biochemical Parasitology*, pp. 257–265.

Avraham Laban et al., (1989) "Transfection of *Leishmania enrietti* and expression of chloramphenicol acetyltransferase gene" vol. 86, *Proc. Natl. Acad. Sci. USA*, pp. 9119–9123.

Angela Cruz et al., (1990) "Gene replacement in parasitic protozoa" vol. 348, *Nature*, pp. 171–173.

Geoffrey M. Kapler et al., (1990) "Stable Transfection of the Human Parasite Leishmania major Delineates a 30–Kilobase Region Sufficient for Extrachromosomal Replication and Expression" vol. 10, *Molecular and Cellular Biology*, pp. 1084–1094.

Avraham Laban et al., (1990) "Stable expression of the bacterial neo' gene in *Leishmania enriettii*" vol. 343, *Nature*, pp. 572–574.

Hein te Riele et al., (1990) "Consecutive inactivation of both alleles of the pim–1 proto–oncogene by homologous recombination in embryonic stem cells" vol. 348, *Nature*, pp. 649–651.

Angela Cruz et al., (1990) "Gene replacement in parasitic protozoa" vol. 348, *Nature*, pp. 171–173.

Jonathan H. LeBowitz et al. (1990) "Development of a stable Leishmania expression vector and application to the study of parasite surface antigen genes" vol. 87, *Proc. Natl. Acad. Sci. USA*, pp. 9736–9740.

Carlos E. Hormaeche, (1991) "Live attenuated salmonella vaccines and their potential as oral combined vaccines carrying heterologous antigens" vol. 142, *Journal of Immunological Methods*, pp. 113–120.

James F. Tobin et al., (1991) "Homologous recombination in *Leishmania enriettii*" vol. 88, *Proc. Natl. Acad. Sci. USA*, pp. 864–868.

Angela Cruz et al., (1991) "Double targeted gene replacement for creating null mutants" vol. 88, *Proc. Natl. Acad. Sci. USA*, pp. 7170–7174.

Cara M. Coburn et al., (1991) "Stable DNA transfection of a wide range of trypanosomatids" vol. 46, *Molecular and Biochemical Parasitology*, pp. 169–180.

James F. Tobin et al., (1992) "A Sequence Insertion Targeting Vector for *Leishmania enriettii*" vol. 267, *The Journal of Biological Chemistry*, pp. 4752–4758.

(List continued on next page.)

*Primary Examiner*—Deborah J. R. Clark
*Assistant Examiner*—Eleanor Sorbello
(74) *Attorney, Agent, or Firm*—Testa Hurwitz & Thibeault, LLP

(57) ABSTRACT

Disclosed herein are novel medical devices, particular well-suited for sustained delivery of therapeutically-significant substances. Also disclosed are methods of making and using these delivery devices. Using these devices and methods, the present invention teaches sustained, targeted and reversible delivery of immunostimulating agents, as well as therapeutic agents such as enzymes, hormones and neurotransmitters, to name but a few.

6 Claims, No Drawings

OTHER PUBLICATIONS

James F. Tobin et al., (1993) "Mutational analysis of a signal sequence required for protein secretionin *Leishmania major*" vol. 62, *Molecular and Biochemical Parasitology*, pp. 243–250.

Kami Kim et al., (1993) "Gene Replacement in *Toxoplasma gondii* with Chloramphenicol Acetyltransferase as Selectable Marker" vol. 262, *Science*, pp. 911–914.

D. Jefferies et al., (1993) "The ble resistance gene as a new selectable marker for *Trypanosoma brucei*; fly transmission of stable procyclic transformants to produce antibiotic resistant bloodstream forms" vol. 21, *Nucleic Acids Research*, pp. 191–195.

Daniel J. Freedman et al., (1993) "Two more independent selectable markers for stable transfection of Leishmania" vol. 62, *Molecular and Biochemical Parasitology*, pp. 37–44.

James F. Tobin et al., (1993) "Transfected Leishmania Expressing Biologically Active IFN–$\gamma^1$" vol. 150, *The Journal of Immunology*, pp. 5059–5069.

Renu Goonewardene et al., (1993) "Transfection of the malaria parasite and expression of firefly luciferase" vol. 90, *Proc. Natl. Acad. Sci. USA*, pp. 5234–5236.

Barbara Papadopoulou et al., (1994) "Changes in Folate and Pterin Metabolism after Disruption of the Leishmania H Locus Short Chain Dehydrogenase Gene" vol. 269, *The Journal of Biological Chemistry*, pp. 7310–7315.

Frederico J. Gueiros–Filho et al., (1994) "On the introduction of Genetically Modified Leishmania outside the Laboratory" vol. 78, *Experimental Parasitology*, pp. 425–428.

Richard G. Titus et al., (1995) "Development of a safe live Leishmania vaccine line by gene replacement" vol. 92, *Proc. Natl. Acad. Sci. USA*, pp. 10267–10271.

Jay Srinivasan et al., (1995) "Effect of the Route of Immunization Using Recombinant Salmonella on Mucosal and Humoral Immune Responses", *Vaccines*, pp. 273–280.

Wen Wei Zhang et al., (1995) "The expression of biologically active human p53 in Leishmania cells: a novel eukaryotic system to produce recombinant proteins", vol. 23, *Nucleic Acids Research*, pp. 4073–4080.

Myra B Kurtz et al.,"Isolation of Hem3 mutants from Candida albicans by sequential gene disruption" vol. 217, *Mol Gen Genet*, pp. 47–52 (1989).

Craig M. Wilson et al., "Amplification of a Gene Related to Mammalian mdr Genes in Drug–Resistant *Plasmodium falciparum*" vol. 244, *Science*, pp. 1184–1186 (Jun. 1989).

Michael J. Mahan et al., "Selection of Bacterial Virulence Genes That Are Specifically Induced in Host Tissues" vol. 259, *Science*, pp. 686–688 (Jan. 1993).

Larry M. Chow et al., "Cloning and functional analysis of an extrachromosomally amplified multidrug resistance–like gene in *Leishmania enriettii*" vol. 60, *Molecular and Biochemical Parasitology*, pp. 195–208 (1993).

Michael J. Mahan et al., "Selection for Bacterial Genes That Are Specifically Induced in Host Tissues: The Hunt for Virulence Factors" vol. 2, *Infectious Agents and Disease*, pp. 263–268 (1994).

Albert Descoteaux et al., "A Specialized Pathway Affecting Virulence Glycoconjugates of Leishmania" vol. 269, *Science*, pp. 1869–1872 (1995).

PCT International Searching Authority, International Search Report (PCT Article 18 and Rules 43 and 44).

Angela Cruz et al., (1990) "Gene replacement in parasitic protozoa" vol. 348, *Nature*, pp. 171–173.

Angela Cruz et al., (1991) "Double targeted gene replacement for creating null mutants" vol. 88, *Proc. Natl. Acad. Sci. USA*, pp. 7170–7174.

LeBowitz et al., "Development of a stable Leishmania expression vector and application to the study of parasite surface antigen genes" vol. 87, *Proc. Natl. Acad. Sci. USA*, pp. 9736–9740 (Dec. 1990).

Richard G. Titus et al., (1995) "Development of a safe live Leishmania vaccine line by gene replacement" vol. 92, *Proc. Natl. Acad. Sci. USA*, pp. 10267–10271.

Gueiros–Filho et al., "Construction of a Leishmania major DHFR–TS knock–out without selectable markers and its use for live vaccination", *Molecular Parasitology Meeting*, (Sep. 17, 1995).

Gueiros–Filho et al., ""In vivo" transposition in Leishmania," *Molecular Parasitology Meeting*, (Sep. 15, 1996).

Gueiros–Filho et al., "Selection against the Dihydrofolate Reductase–Thymidylate Synthase (DHFR–TS) Locus as a Probe of Genetic Alterations in *Leishmania major*", *Molecular and Cellular Biology* (Oct. 1996, p. 5655–5663).

Curotto de Lafaille et al., "Creation of Null/+Mutants of the α–Tubulin Gene in *Leishmania enrietti* by Gene Cluster Deletion", *The Journal of Biological Chemistry*, (Nov. 25, 1992 p. 23839–23846).

Donald et al., "Insertional mutagenesis and marker rescue in a protozoan parasite: Cloning of the uracil phosphoribosyltransferase locus from *Toxoplasma gondii*", *Proc. Natl. Acad. Sci USA*, (Jun. 1995 p. 5749–5753).

Donald et al., "Insertional Tagging, Cloning and Expression of the *Toxoplasma gondii* Hypoxanthine–Xanthine–Guanine Phosphoribosyltransferase Gene", *The Journal of Biological Chemistry*, (Jun. 14, 1996, p. 14010–14019).

Hwang, et al. "Creation of Homozygous Mutants of *Leishmania donovani* with Single Targeting Constructs", *The Journal of Biological Chemistry*, (Nov. 29, 1996, p. 30840–30846).

Cruz, A. et al. Double targeted gene replacement for creating null mutants, Proc. Natl. Acad. Sci. USA. 1991 vol. 88, pp. 7170–7174.*

Verma, et al. Gene therapy–promises problems and prospects: Nature vol. 389,p. 239–241 Sep. 1997.*

Miller et al. Targeted vectors for gene therapy; The FASEB journal,vol. 9. Feb. 1995, p. 190–199.*

Deonarain, et al. Ligan–targeted receptor–mediated vectors for gene delivery; Exp. Opin. Ther. Patents, vol. 8(1) p. 53–69.*

Crystal, .R. , Transfer of genes to Humans: Early Lessons and obstacles to success: Science vol. 270,p. 404–410. Oct. 1995.*

Alberts et al. Molecular Biology of the cell, third edition, Garland Publishing, Inc. p. 511.*

\* cited by examiner

SUSTAINED DELIVERY DEVICE AND METHODS OF MAKING AND USING THE SAME

REFERENCE TO RELATED APPLICATIONS

The present application is a continuation of U.S. Ser. No. 08/735,507, filed on Oct. 23, 1996, issued as U.S. Pat. No. 6,020,144, which claims priority to a provisional patent application, U.S. Ser. No. 60/026,006, filed on Sep. 12, 1996, the disclosure of which is incorporated by reference herein.

GOVERNMENT SUPPORT

Work described herein was supported, in part, by Federal Grant No. NIH AI 29646 and AI 21903, awarded by the National Institutes of Health. The Government has certain rights in the invention.

FIELD OF THE INVENTION

This invention relates generally to the field of medical devices, and more particularly, to methods and compositions for sustained delivery of therapeutically-significant substances.

BACKGROUND OF THE INVENTION

A number of diseases are caused by disorders in cellular metabolism. For many of these diseases the nature of the metabolic defect has been identified, and the rapid progress of biomedical research continues to further our understanding of the precise mechanisms involved. For example, Type I diabetes is known to result from defective glucose metabolism associated with decreased levels of insulin, whereas different cancers are due to defective control of cellular division and proliferation associated with mutations in a variety of cellular genes, many of which have been identified. Many disorders in cellular metabolism are caused by somatic or hereditary genetic mutations which result either in inappropriate expression of a given gene product or expression of a defective gene product. However, environmental assaults such as chemical poisoning, physical damage or biological infection can also result in specific defects in cellular metabolism. In addition, cellular aging often results in metabolic disorders. Understanding the nature of a given metabolic disorder identifies targets/goals for an effective treatment.

A traditional approach to treatment consists of administering systemically, to a patient, a pharmaceutical compound or drug that overcomes the metabolic disorder. For example, administering exogenous insulin to a patient alleviates the symptoms of Type I diabetes. There are, however, several drawbacks to this type of drug therapy. For a pharmaceutical compound to be effective, it must be administered so that it reaches its site of action at an appropriate concentration. If the compound is provided systemically, whether administered orally or by injection, undesirable side effects may be caused by the systemic levels of the compound required for it to be effective at its site of action. This is the case for many chemotherapeutic agents used to treat various forms of cancer. Current attempts to overcome this problem consist of trying to target pharmaceutical compounds to their desired site of action for sustained periods of time at effective concentrations. There is not yet a reliable and general method for such targeted drug delivery.

An additional problem with traditional drug administration is that the drug must be stable and transportable to its site of action. For many diseases, the most appropriate therapeutic compound would be a specific protein, especially if the disease results from the absence of a functional form of that protein. However, delivering any given protein to its desired site of action can be complicated by its susceptibility to denaturation and proteolytic degradation, and by poor mobility to its desired site of action.

An alternative approach is gene therapy which attempts to overcome these problems by circumventing the requirement of transporting a protein to its site of action. The goal of gene therapy is to provide DNA encoding the desired protein to the site of action. The DNA then is transcribed and translated to produce the protein in therapeutically effective concentrations at the appropriate site in the body. However, gene therapy also faces a delivery problem of how to get the DNA to the appropriate cells. Current approaches to solving this problem consist of using viral vectors, liposome encapsulation, direct injection, or complexation with carrier proteins. At present, none of these approaches provides an effective and general method for getting DNA to any desired site of action within the body. Current gene therapy technology also does not address the required duration of therapy. Hereditary diseases, for example, might require constant therapy to correct the inherited metabolic disorder. On the other hand, cancer treatment may only be needed for a time sufficient to destroy the cancer cells.

There is, therefore, a need in the art for effective devices and methods for delivering physiologically useful compounds to any desired site of action, in a controlled fashion. It is an object of the present invention to provide such devices and methods.

SUMMARY OF THE INVENTION

A novel approach to the delivery of drugs and other therapeutic substances has now been discovered. The present invention uses genetic mutations to exploit certain innate characteristics of a group of unicellular organisms known as protozoa. By genetically modifying these organisms in accordance with the present invention, the skilled practitioner can now use these organisms as improved devices for the sustained delivery of drugs and other substances.

The rationale for using these organisms as delivery devices includes the following: First, these organisms have evolved a sophisticated ability to infect a host and evade their host's immune defenses. Consequently, these organisms can persist in their host in an undetected and undisturbed state for long periods of time. As taught herein, this characteristic can be exploited to achieve sustained, in vivo delivery of a drug or other therapeutic. Moreover, by practicing the genetic manipulations disclosed herein, an organism's ability to persist in its host can be closely controlled. In fact, an organism can be engineered so that it can be subsequently eliminated on demand. Furthermore, the number of organisms in the host as well as the dose of drug or substance delivered to the host can also be closely controlled using the present invention.

Second, these organisms have evolved very specific, natural tissue preferences. Consequently, these organisms reside and persist in specific tissues in their respective hosts. Moreover, protozoa as a group reside in virtually every tissue or organ of vertebrates and invertebrates. As taught herein, this characteristic can be exploited to achieve targeted, tissue-specific delivery of a drug or other therapeutic substance. Currently, the only available type of targeted, sustained in vivo delivery relies on gene therapy, however, gene therapy cannot be similarly controlled, is often viral-vector mediated, and can result in undesirable and/or permanent alteration of the recipient's genome. Thus, the teachings of the present invention overcome the limitations of gene therapy, as well as overcome numerous problems associated with more conventional drug therapy methods, such as unnecessary systemic exposure, toxicity, poor transportability, degradation and stability to name but a few.

Accordingly, the teachings of the present invention provide a device for delivery of a drug or therapeutic substance which is sustained, targeted, reversible and virus-free, without necessarily exposing the recipient to permanent genetic alterations. In one aspect, the present invention features a sustained delivery device comprising an isolated, conditionally defective unicellular organism expressing a therapeutically-significant substance. The genome of this organism is genetically altered to lack a naturally-occurring nucleotide sequence defining a genetic locus responsible for a selectable phenotype, and encode an expression product for sustained delivery. In some embodiments, the unicellular organism is a diploid organism. In other embodiments, the organism is an asexual diploid organism. In certain currently preferred embodiments, the organism is a protozoa, more preferably a parasitic protozoa. The expression product of the present device can be encoded by a heterologous gene. Currently preferred are genes encoding a hormone, enzyme or neurotransmitter, however, any substance of therapeutic significance is contemplated. In other embodiments disclosed herein, the device can comprise an exogenous marker gene. For purposes explained herein, a currently preferred selectable phenotype is one associated with a conditional defect in metabolic function such as, but not limited to, conditional auxotrophy.

In yet another currently preferred embodiment, the above-mentioned conditionally defective organism has a selectable phenotype due to the excision of a naturally-occurring genetic locus from its genome. In this embodiment, the organism is a transfectant, the genome of which comprises transfected DNA including a nucleotide sequence free of a marker gene and which is complementary to a wild-type nucleotide sequence flanking the locus in the wild-type organism, wherein the genetic locus is excised by homologous recombination with the transfected DNA. In a most currently preferred embodiment, the transfected DNA further comprises a nucleotide sequence defining a heterologous gene. Additionally, the present invention contemplates that a selectable phenotype can be generated by other genetic alterations such as, but not limited to, alterations achieved using transposon technologies. Typically, transposons cause loss of a genetic locus by interrupting the naturally-occurring nucleotide sequence, which can generate a selectable phenotype suitable for use with the present invention.

In a second aspect, the invention features a method of providing sustained delivery of an expression product to a host comprising the step of administering any one of the above-described sustained delivery devices to the host. In a currently preferred embodiment, the method of the invention further involves the step of controlling the detectable amount of device comprising the above-described organisms or expression product produced by the organisms. A currently preferred host is a mammal, although the present invention contemplates that any metazoan organism is a suitable host, including plants, insects and mammals.

In a third aspect, the invention features a method for producing any one of the above-described sustained delivery devices. The currently preferred method comprises the steps of excising a naturally-occurring genetic locus from the genome of a unicellular organism. This can be accomplished by transfecting the organism with DNA comprising nucleotide sequences complementary to wild-type sequences flanking the locus under conditions which promote excision of the locus, and then selecting for a conditionally defective phenotype generated by loss of the genetic locus. In a preferred embodiment particularly useful for delivery of a therapeutic substance, the transfecting step contemplates transfecting with DNA further comprising a heterologous gene. As described above, this heterologous gene can encode any therapeutically-significant substance such as, but not limited to, an enzyme, hormone or neurotransmitter. In another currently preferred embodiment, the transfecting step involves transfecting with DNA further comprising an exogenous marker gene. Yet another preferred method relies on transposon technologies to induce the loss of a genetic locus and the appearance of a selectable phenotype. It is understood that that any device prepared in accordance with these methods is within the scope of the present invention.

In short, the invention provides the art with a heretofore unappreciated method of producing unique devices for sustained delivery of therapeutically-significant products to a mammal. Moreover, in accordance with present teachings, these delivery devices can be controlled to provide effective dosages of immunostimulators and/or expression products with therapeutic/pharmaceutical benefits. Furthermore, these delivery devices can be targeted to specific tissues. Finally, as will be appreciated by the skilled artisan, the devices and methods of making and using the same disclosed herein can be used in human medical and veterinary applications, as well as insect and plant applications.

These and other objects, along with advantages and features of the invention disclosed herein, will be apparent from the description and claims that follow.

DETAILED DESCRIPTION OF PREFERRED EMBODIMENTS

In its broadest aspects, the present invention provides the skilled artisan with the analytical tools and technical know-how sufficient to isolate conditionally defective organisms that can provide a delivery platform, preferably a sustained delivery platform, for therapeutically-significant genes and/or their expression products.

On the one hand, the skilled artisan will recognize that the delivery device of the instant invention can be exploited for its immunoprotective potential per se. In a related embodiment, the instant delivery device can be modified to enlarge or improve its inherent immunoprotective potential, such as by enabling the device to further express immunodominant or protective antigens, lymphokines or immunomodulatory substances. On the other hand, the present delivery device can also be used as a platform for administration of immunoprotective substances relevant to diseases induced by other, unrelated infectious agents or organisms. Still further, the skilled artisan will recognize that the present delivery device can be exploited as a general-purpose delivery platform by means of which any heterologous gene and/or its expression product can be provided to a host. Guidance provided herein accordingly will facilitate evaluation of diverse organisms as sustained delivery vehicles, thereby broadening the spectrum of potential therapeutic tools for amelioration and/or treatment of diseases.

In order to more clearly and concisely describe the subject matter of the claimed invention, the following definitions are intended to provide guidance as to the meaning of specific terms used in the following written description, examples and appended claims.

As used herein, the term "organism" includes any unicellular organism suitable for use in the devices and methods of the present invention. Haploid and diploid, including asexual diploid, unicellular organisms are contemplated. Particularly preferred unicellular organisms include protozoa, especially parasitic protozoa Set forth below is a non-limiting list of those unicellular protozoa contemplated to be within the scope of the present invention. Also set forth below is a discussion of generally preferred features and characteristics of the unicellular organisms most suitable for use in the present invention. As exemplified in Examples 2 and 8, respectively, two diploid genera currently preferred are Leishmania and Trypanosoma. Most currently preferred are the species *L. major, L. tropica, L. aethipica, L. enrietti, L. panamaenisis, L. guyanensis, L. donovani, L. chagasi, L. infantum, T. cruzi, T. brucei* and members of the trypanosomatid genus Endotrypanum such as *E. monterogei* and *E. schaudinni*. As also exemplified in Example 8, a currently preferred haploid genus is Toxoplasma; a most currently preferred species is *T. gondii*. Other currently preferred haploid genera include Plasmodium, Eimeria, and Cryptosporidia. A currently preferred genus of uncertain ploidy is Giardia. A most currently preferred species is *G. lamblia*. Other preferred genera of uncertain ploidy include Entamoeba, Acanthamoeba and Naegleria, and Microspoidia and Trichomona (*T. vaginalis* and *T. foetus*, in particular) generally.

The methods of the present invention permit production and isolation of a "conditionally defective" unicellular organism. For purposes of the present invention, a conditionally defective organism must comprise a "selectable phenotype," i.e., a phenotype generated by a genetic modification which permits identification and isolation of such an organism without resort to, or reliance on, markers encoded by exogenous genes. That is, a genetic modification has rendered it metabolically, nutritionally, reproductively, immunologically, pathogenically, and/or secretion disabled or dysfunctional relative to the wild-type organism. As contemplated herein, a conditionally defective organism is a genetically-modified unicellular organism whose tissue-specificity, growth and/or viability can be modulated by manipulating the conditions in which it is maintained, propagated and/or passaged. Consequently, one conditionally defective organism of the present invention can be dependent upon an exogenously provided substance or condition. Alternatively, in other embodiments, the organism is dependent upon the absence or lack of a particular substance or condition. As disclosed herein in Examples 2, 3, 5 and 7, this conditional disablement or defect can be exploited to the practitioner's advantage. It will be understood that any genetic modification which gives rise to a selectable phenotype is within the scope of the present invention. Two currently preferred genetic modifications are described herein below, but are intended to be exemplary only.

In certain embodiments of the present invention, the above-described genetic modification is removal or excision of a genetic locus. The term "genetic locus" is intended to include any nucleotide sequence, including a single nucleotide, within the genome of a unicellular organism. Preferably, a genetic locus corresponds to at least one allele of a gene. As exemplified below, a genetic locus can also preferably correspond to two alleles of a gene. The skilled artisan will appreciate the circumstances under which this distinction is operative. As already stated, removal or excision of a genetic locus is accomplished by transfecting the organism with DNA comprising sequences complementary to the naturally-occurring nucleotide sequences flanking either end of a genetic locus. The extent to which the transfecting sequences are complementary to the naturally-occurring sequences can vary. All that is required is that the transfecting sequences be complementary enough to permit a recombination event, for example homologous recombination, to occur. Similarly, the precise length of the flanking sequences can also vary. Again, all that is required is that the flanking sequences be of sufficient length to permit a recombination event to occur. Flanking sequences 400 bp long are effective, and sequences that are longer or shorter will also be effective. The skilled artisan will appreciate these fundamentals and can prepare suitable transfecting flanking sequences using only routine experimentation. Furthermore, only routine efforts are required to determine the primary nucleotide sequence of the DNA flanking either end of the genetic locus. Once the skilled artisan has selected the particular genetic locus which is to be removed or excised, the flanking sequences can be isolated by routine methods and their primary nucleotide sequence deduced by routine methods. For the purpose of this invention, it is understood that the extent of physical removal or excision of a nucleotide sequence comprising a particular genetic locus need only be enough to confer on the organism a selectable phenotype as defined herein.

Other embodiments of the present invention contemplate unicellular organisms rendered conditionally defective by interrupting, or otherwise disrupting, a naturally-occurring genetic locus. Methods of achieving such interruptions or disruptions using transposons are exemplified below in Example 4. Again, it is understood that the extent of, or precise manner of, physical interruption of a nucleotide sequence comprising a particular genetic locus need only be enough to confer on the organism a selectable phenotype. As used herein, the term "transposon" refers to a discreet genetic element that insures its own maintenance by inserting into other autonomously maintained genetic elements. Transposons can be constructed to further encode substances of particular interest, for example a heterologous gene encoding an expression product of therapeutic interest. Transposons are useful tools for genetic manipulations such as deletions, inversions, and fusions, as is well known in the art. A transposon is a specific DNA segment with the ability to move as a unit in more or less random fashion from one genetic locus to another. Exemplary of specific transposons which may be used herein are transposons originally derived from insects, preferably members of the Tcl/mariner family, most preferably the mariner transposon element from Drosophila. As disclosed herein in Example 4, insertional inactivation mediated by a transposon can be a powerful way to generate mutants and gene fusions which would facilitate studies of gene function in an asexual diploid like Leishmania. The development of a mariner-based heterologous transposon system is a significant addition to the array of tools available for dissecting the genetic basis of relevant aspects of Leishmania biology, such as virulence and pathogenesis. The same system can be developed to ameliorate the restrictions of other asexual diploids using methods within the scope of the present invention.

As already explained, a "selectable phenotype" includes any phenotype generated by genetic modifications as described herein. That is, the present invention contemplates that a selectable phenotype arises upon loss of a naturally-occurring nucleotide sequence defining a genetic locus, preferably an allele, alternatively a gene. All that is required is that the resultant phenotype permits the skilled practitioner to identify and isolate the appropriately modified organism. A generalized discussion of selection paradigms and several examples of selectable phenotypes are set forth below. Currently preferred selectable phenotypes include conditional auxotrophy. An exemplary conditional auxotroph lacks all wild-type alleles of the DHFR-TS locus (for example, one allele in a haploid organism, and two alleles in a diploid organism). Other currently preferred selectable phenotypes include those associated with a conditional defect in metabolic function such as, but not limited to, nucleotide synthesis, metabolism or regulation. Still others are described hereinbelow.

As used herein, positive and negative selections are contemplated to select for and against the presence of a given genetic locus to the extent that the genetic locus is associated with a phenotype for which a positive or negative selection exists. A "positive selection" for a given phenotype is defined herein as a method of implementing a set of conditions wherein only cells that express the phenotype are isolated. A "negative selection" against a given phenotype is defined herein as a method of implementing a set of conditions wherein only cells which do not express the phenotype are isolated. A "negative selection" therefore selects against the presence, or for the absence, of the genetic locus associated with the phenotype. A genetic locus against which a negative selection can be applied is defined herein as a genetic locus which can act as a "negative marker." It will be understood that a "positive marker" is defined analogously.

As exemplified herein in Example 2, the present invention permits isolation of a conditionally defective unicellular organism comprising a selectable phenotype without requiring reliance on exogenous marker genes. A "marker gene" includes any exogenous gene introduced via transfecting or transforming DNA sequences as disclosed herein, which is relied upon to identify and isolate a conditionally defective organism having a selectable phenotype as defined herein. As used herein, "marker genes" such as exogenous antibiotic-resistance genes are genes generally considered by the art to be useful to monitor, identify and thereafter isolate genetically modified organisms. A "marker gene" falls within the broad definition of positive marker set forth above. Generally, such genes have heretofore been relied on in diploid organisms because no other selectable phenotype was appreciated or recognized. As demonstrated by the present invention, phenotypes can be generated and selected independently of exogenous marker genes. It is understood that the presence of a marker gene(s) per se does not affect exploitation of conditionally defective organisms as sustained delivery devices as exemplified below.

The term "sustained delivery device" means a device which comprises an isolated, conditionally defective organism, the genome of which lacks a naturally-occurring nucleotide sequence defining a genetic locus or a gene encoding a selectable phenotype. In certain preferred embodiments, the genome comprises a heterologous gene of interest. The genome can optionally further comprise an exogenous marker gene. It is understood that the sustained delivery device can be used at least to immunostimulate and/or deliver a therapeutically-significant substance to a host organism. In certain embodiments, a device can both immunostimulate and deliver a desired substance. Sustained delivery of an immunostimulating agent/or a therapeutic substance can be achieved using the devices of the present invention. The term "sustained" means of a period of time sufficient to at least achieve immunostimulation or expression of a desired substance in a host. In certain preferred embodiments, the present delivery device can persist in the host for whatever period of time is clinically required. As also. exemplified herein, sustained delivery can be accomplished by exploiting the organism's conditional defect, such as by providing or depriving the host of a substance which can control the viability or biological competence of the organism. Exemplification of the foregoing can be found in Examples 5, 6, 7, and 8. Also contemplated is a type of sustained delivery which can be autoregulated by the organism. This is exemplified in Example 9.

In certain preferred embodiments, the sustained delivery device further comprises a "gene of interest," most preferably a heterologous gene encoding an expression product of interest. "Heterologous" means not naturally-occurring in the genome of the organism, including gene copy number. Numerous such genes and their expression products within the scope of this invention are listed below. As used herein, "expression product" means any product expressed by the organism, the sustained delivery of which is desired. An expression product can be encoded by a homologous gene, i.e., a gene which is naturally-occurring in the organism, or an expression product can be encoded by a heterologous gene as already explained. An example of a desirable expression product encoded by a homologous gene is an expression product which makes the organism per se a suitable immunostimulating agent or vaccine. Thus, it is understood that the term expression product is not limited in its use herein. When required, expression products can be detected using routine means available in the art. Expression products contemplated herein include, but are not limited to: DNAs, RNAs, oligonucleotides, proteins, peptides, carbohydrates, lipids, nucleosides, amino acids, steroids, fatty acids, vitamins and antibiotics including anti-viral substances. It is understood that heterologous genes can be introduced into the genome concomitantly with, or independently of, the transfecting or transforming sequences described above. Additionally, a heterologous gene can reside on a plasmid and be introduced thereby.

As used herein, the term "immunostimulate" means to stimulate the immune system of the recipient. Immunostimulation results in one or more functions within the immune system being induced or increased and, in certain embodiments, directed towards an immunostimulating agent. Immunostimulating agents include agents such as conventional vaccines, or the vaccine-type devices disclosed herein in Examples 5 and 6. By way of example only, immunostimulation can be measured by the production of antibodies. As used herein, "vaccine" is understood to mean any substance, device or agent used to stimulate the immune system of a living organism so that some protection against future disease and/or harm is provided, even if transiently. Immunization refers to the process of inducing antibodies and/or cellular immune responses. It is understood that vaccine-type devices of the nature disclosed and exemplified herein are likely to produce a broad range of immune responses in addition to immunoglobulin production, for example, cellular and humoral immunity.

In their broadest applications, the "null-targeting" methods of the invention can be used to generate homozygous deletions of any genetic locus against which negative selection can be applied. Null-targeting refers to the process of removing a genetic locus, for example by homologous gene replacement, using appropriate constructs lacking the genetic locus, such that no DNA necessarily replaces the removed locus. A preferred aspect of the invention is that homozygous deletions can be generated without the concomitant introduction of any exogenous marker gene, into the chromosomal site of the deletion. A negative selection can be applied against a genetic locus if the genetic locus is responsible for (or encodes) a phenotype against which a negative selection exists or can be implemented. Using methods of negative selection against a given phenotype comprises implementing a set of conditions under which cells can be isolated and subsequently grown as clonal populations of cell which do not express the phenotype. As a general example, a negative selection against the phenotype of expressing a given gene product comprises exposing cells to conditions that allow the isolation of cells which do not express the gene product. The isolated cells can subsequently be grown as clonal populations of cells which do not express the gene product.

The following non-limiting general examples of phenotypes and negative selections will guide the artisan of ordinary skill in the practice of methods according to the invention. It is understood that in the following examples, the phenotypes are non-essential phenotypes; that is, the absence of the phenotype is not lethal to the cells under the conditions of the negative selection. Expression of a given metabolic enzyme can be selected against by growing cells in the presence of a compound that, when metabolized by the enzyme, becomes toxic and kills the cells. Under these conditions, only cells which do not express the enzyme, and therefore do not metabolize the compound, will grow. Expression of a given metabolic enzyme can also be selected against by growing cells in the presence of a compound that, when metabolized by the enzyme, imparts an observable phenotype to the cells, for example a specific color or fluorescence. Under these conditions, only cells which do not express the enzyme are non-colored or non-fluorescent. These cells can be identified and isolated by methods well known in the art, such as growing under conditions allowing the formation of isolated colonies, or by fluorescence activated cell sorting. In a related example, selection against a given metabolic enzyme can be accomplished by growing cells under conditions which alter the function of the enzyme in such a way that deleterious or lethal metabolites accumulate in the cells. Under these conditions, only cells that do not express the enzyme will grow well, and these cells can thereby be isolated using methods known in the art. These examples therefore allow cells which do not express the enzyme to be isolated from cells which do express the enzyme. A further general example of a negative selection comprises identifying cells which do not express a given antigenic product. This can be accomplished using colony blotting and Western blotting procedures well known in the art. Yet another general example comprises cell-surface markers and marker-specific antibodies conjugated with toxins.

The following non-limiting examples of genes can be used as negative markers according to methods of the invention: adenine (APRT), hypoxanthine/guanine (HGPRT), hypoxanthine/guanine/xanthine (HXGPRT), uracil phosphoribosyl transferase (UPRT), dihydrofolate reductase-thymidine synthetase (DHFR-TS), thymidine kinase (TK) and orotodine 5'-phosphate- decarboxylase. These markers can be selected against using methods known in the art which illustrate some of the general principles of negative selection described above. A specific example of using DHFR-TS as a negative marker for null-targeting in Leishmania is provided in Example 2.

The null-targeting methods of the invention are not limited to phenotypes against which a negative selection can be applied. According to methods of the invention, it is possible to generate null-targeted deletions of any locus on the chromosome, provided that the deletion is not lethal to the cell. The method comprises the step of first introducing a known negative marker into the locus at which a null-targeted deletion is desired. This is achieved by transfecting the cell with a linear piece of DNA comprising a negative marker, a positive marker and flanking sequences which are complementary to sequences flanking the genetic locus to be deleted. Positive selection for the positive marker is used to isolate cells in which the transfected DNA has undergone homologous recombination with the chromosomal DNA, resulting in the targeted locus being replaced by the positive and negative markers. In a second step, the null-targeted deletion is generated according to methods described herein. Specifically, the isolated cell line, containing both the positive and negative markers, is transfected with DNA comprising the above-mentioned flanking sequences, with no other sequence between the flanking sequences being required. Negative selection against the negative marker is used to isolate null-targeted deletion cells in which the transfected DNA has undergone homologous recombination with the chromosomal DNA, resulting in the positive and negative markers being excised. The positive marker used in this method can be any gene for which a positive selection can be applied, for example any of the drug resistance markers well known in the art. A marker may be used which can act both as a positive marker and as a negative marker. A specific example of the use of this type of marker is provided in Example 3. Alternatively, the positive and negative markers may be different. The positive and negative markers may be derived from the species being null-targeted. Alternatively, one or both of the markers may be derived from a different species of organism. For the marker to be most useful, the organism being null-targeted preferably does not express the phenotype associated with the marker. If, for example, the marker is a gene derived from the species being null-targeted, then the cells used according to this method are preferably deficient in this marker gene, due to a mutation, preferably a deletion in this marker gene. It will be appreciated by the skilled artisan that this method alone or in combination with other methods disclosed herein, and known in the art, can be used to null-target a haploid organism, null target a single allele of a diploid organism, null target both alleles of a diploid organism or null-target any number of alleles of an organism of higher ploidy. Non-limiting examples are provided in Example 8.

Accordingly, the present invention provides the technical know-how to construct and isolate conditionally defective organisms. Such organisms can then be exploited to deliver numerous and functionally varied therapeutic substances. By way of example, the following categories of biotechnology and/or therapeutic substances are contemplated. These categories include: metabolic enzymes, antisense molecules, clotting factors, colony stimulating factors, erythropoietins, growth factors, human growth hormones, interferons, interleukins, monoclonal antibodies, recombinant soluble receptors, tissue plasminogen activators, to name but a few.

More specifically, examples of antisense therapies currently under development suitable for use with the present invention include: HIV antisense, cancer antisense and inflammatory disease antisense. Clotting factors can include recombinant human factors currently under development for treatment of hemophilia A & B. Exemplary colony stimulating factors include: GM-CSF, and rG-CSF currently considered useful for treatment of infectious diseases, hemophiliac disorders, and HIV infection. Among the growth factors, those contemplated herein include the art-recognized compounds known as: transforming growth factor-beta, brain-derived neurotrophic factor, transferrin, insulin-like growth factor, nerve growth factor, neurotrophin-3, recombinant human platelet-derived growth factor-BB, and recombinant insulin-like growth factor-I/ binding protein-3 to name but a few. Human growth hormones include human growth hormone releasing peptide, somatropin for injection, and recombinant variants thereof. The category of interferons include interferon gamma-1b, interferon alfa-n3, gamma interferon, consensus interferon, recombinant interferon beta, to name but a few of the more well described species of interferons. With respect to the interleukins, substances such as liposomal IL-2, recombinant human interleukin-1, recombinant interleukin-2, recombinant human interleukin-3, glycosylated recombinant human interleukin-6, and IL-12 and its natural and synthetic variants, are also contemplated as suitable for use with the present invention.

Currently available and well described monoclonal antibodies useful with the present. invention include: monoclonal antibodies directed to breast cancer, HIV, liver and germ cell cancers, allergic diseases, asthma, metastatic or recurrent colorectal cancer, rheumatoid arthritis, ovarian cancer, gram-negative sepsis, multiple sclerosis, solid tumors, metastatic cancer, leukemia and metastatic melanoma, acute myeloid leukemia, respiratory syncytial virus disease, B-cell lymphomas, B-cell leukemias, T-cell malignancies, small-cell lung cancer, renal diseases, prostate adenocarcinoma, acute CMV disease, to name but a few. Recombinant soluble receptors, for indications such as asthma, treatment of rhinovirus induced common cold, septic shock, severe sepsis, rheumatoid arthritis, multiple sclerosis, respiratory distress syndrome, are contemplated herein.

Other contemplated substances include: recombinant human glucagon, recombinant human follicle-stimulating hormone, insulin, human corticotropin-releasing hormone, insulinotropin, recombinant human leutinizing hormone, recombinant human parathyroid hormone, stem cell factor, recombinant human thyroid stimulating hormone, tissue factor pathway inhibitor, to name but a few. As stated earlier, these particular substances merely illustrate the broad categories of biotechnology and/or therapeutic indications with which the present invention can be practiced, and the invention is not limited to practice therewith. A currently preferred substance is insulin as exemplified in Example 9.

Generally speaking, the devices and methods of this invention can be used to deliver, preferably in a sustained manner, a diverse variety of substances. All categories of ligands, peptides, proteins, lipids, fatty acids, steroids, catacholamines, neurotransmitters, immunostimulants, carbohydrates, amino acids, neurostimulatory factors, human growth factors, and cytokines are contemplated. Any substance deemed to have therapeutic value is contemplated herein. Currently, substances such as insulin, gamma interferon, BMPs, tissue plasminogen activator, beta interferon, Ceredase®, Cerezyme®, erythropoietin, GM-CSF, G-CSF, DNase, and Factor VIII are among the preferred art-recognized substances of current therapeutic interests. Other currently preferred substances would include those suitable for treating the following selected diseases such as, but not limited to, osteoporosis, diabetes, cancer, severe anemia, short stature, and hemophilia Gaucher's disease as treated by Ceredase® (and/or its naturally-occurring and synthetic variants) and diabetes as treated with insulin (and/or its naturally-occurring and synthetic variants) are two currently-preferred disease-therapy paradigms.

It is contemplated that, in view of the human genome initiative, very many more genes of therapeutic value will be sequenced. Consequently, the identification of many proteins with therapeutic value will be forthcoming and are contemplated to be within the scope of the present invention. Particularly preferred substances include, but are not limited to, those biotechnology drugs currently approved for use in humans. Such drugs include: gamma interferon, interferon alpha-N3, recombinant interferon beta I-A, recombinant interferon beta 1-B, recombinant alglucerase, recombinant imiglucerase, CMV immunglobulin, daunorubidin, doxorubicin, somatrophin, recombinant human insulin, alpha-interferon, yeast derived GM-CSF, pegaspargase, human growth hormones, DNase, recombinant antihemophilic factor, recombinant hepatitis B, to name but a few.

As exemplified herein, the present invention also provides a method for delivering a gene of interest to a mammal. Numerous heterologous genes have been identified in the art and their delivery to a patient can be accomplished using the methods and devices of the present invention. For example, gene delivery in accordance with the present invention can be used to treat the following indications: cystic fibrosis, sinusitis, HIV, colon cancer, metastatic renal cell carcinoma, disseminated malignant melanoma, neuroblastoma, Gaucher's disease, breast cancer, melanoma, non-small cell lung cancer, and clinical equivalents thereof. A currently preferred disease is Gaucher's disease as exemplified in Example 9.

As exemplified herein in Example 5, the present invention also provides a device for delivering an immunostimulant to a mammal. In certain embodiments, this immunostimulating property of the instant device serves to vaccinate the recipient. Accordingly, the present invention can serve as an improvement for a conventional vaccine for the following diseases and/or conditions: pediatric pertussis, HIV infection, multiple sclerosis, melanoma, breast cancer, diarrheal diseases and gastritis, CMV virus, prostate and ovarian cancers, diphtheria, tetanus, cancers such as colorectal, stomach, and pancreatic, peptic ulcers, melanoma, hepatitis B, herpes simplex, influenza, psoriasis, lyme disease, infectious diseases generally, respiratory syncytial virus, and various protozoa and parasitic protozoa such as Leishmania, to name but a few.

Additionally, it will be appreciated by the skilled artisan that this invention also provides methods and devices for desensitizing an organism to an allergen. By way of example, sustained delivery devices can be constructed to express or produce an allergen. As used herein, allergens are substances that cause allergic reactions. It will be appreciated that many different materials are allergens such as, but not limited to, animal dander and pollen. It is possible to induce tolerance to an allergen in an organism that normally shows an allergic response. Methods of inducing tolerance are well known and generally comprise administering allergen to the organism in increasing dosages. Thus, in one further embodiment, when the immunostimulating component of the delivery device is an allergen of the host, the present invention permits the skilled practitioner to develop an exposure regimen designed to specifically desensitize the allergic host. It is contemplated that embodiments of this nature can also be used to desensitize an auto-allergic response in an organism afflicted with auto-immune disease.

As already stated, the preferred organism of the present invention is a unicellular organism. In certain embodiments, a diploid organism is preferred; in others, a haploid organism. Currently, one of the preferred unicellular organisms is a protozoa. According to M. A. Sleigh (1991 *Parasitic*

*Protozoa*, 2nd edition, volume 1, pages 1–53, eds. J. P. Kreier & J. R. Baker; Academic Press, Inc., New York), protozoa can be categorized by certain distinguishing structural characteristics. The four phylum are: Sarcomastigophora which includes organisms having pseudopodia or flagella as locomotor organelles, including the amoebae and flagellate protozoan parasites. Ciliophora includes organisms bearing cilia; Apicomplexa includes a large and diverse group of organisms including the intestinal, blood, and tissue dwelling coccidians; and finally, Microspora includes spore forming organisms, among which are human parasites.

Among the flagellate protozoa, there is a subgroup called kinetoplastids (trypanosomes and their allies). Most of the 600 or so species of kinetoplastids are parasites, including important genera such as Trypanosoma and Leishmania which parasitize vertebrates, including humans. These genera are among two of the currently preferred genera of diploid organisms suitable for practice with the instant invention. Other genera can be found as gut parasites in insects and as parasites in plants. Accordingly, members of such genera can be used to practice the instant invention when the desired host is an insect or a plant. Among those spore forming groups of protozoa, there are three subcategories. They include microspora, sporozoa, and mixospora. The microspora are intracellular parasites. There are a number of microspora genera which parasitize invertebrates such as Encephalitozoon in mammals, including humane with immune deficiency, and Glugea in fish. Another wide spread genera is Nosena, the species of which cause important diseases in insects of economic importance such as bees and silk worms. Again, in applications involving hosts such as non-human vertebrates or insects, the delivery device of the present invention can be exploited most successfully. Among the sporozoa category, there are numerous intestinal, blood, and tissue dwelling coccidians suitable for use with the present invention. Particularly useful coccidians include Cryptosporidium, Isospora, Toxoplasma, Sarcocystis, and Plasmodium. Certain species of genera of Eimeria and Isospora are important pathogens of domestic animals. Toxoplasma is a widely distributed parasite of mammals that is now regarded by certain artisans as a member of the genes Isospora. Toxoplasma is a currently preferred haploid genera suitable for use with the present invention. Finally, members of the subcategory mixospora include protozoa commonly considered parasitic of fish. For example, it is currently believed that a member of the mixospora category is responsible for "whirling disease" in trout. The skilled artisan will appreciate that the instant invention would be applicable to control such a disease.

While a generally useful feature of currently preferred organisms is that they can be cultured in vitro, this is not a requirement. Among the above-referenced diploid genera, two currently preferred are Leishmania and Trypanosoma, both blood and tissue flagellates reside in humans. Both genera can, in certain stages of their life cycle, be propagated in culture. Moreover, numerous aspects of the molecular biology of protein processing and expression have been studied in these genera. Features shared with higher eucaryotes include synthesis of capped polyadenylated cytoplasmic RNA; a typical ribosome and protein synthetic apparatus; and, a general protein secretory apparatus including endoplasmic reticulum, golgi apparatus and exo- and endocytosis.

In the genera Leishmania, several species can cause visceral disease and reside intracellularly, for example, in lymph nodes, liver, spleen, bone marrow, etc. Other species of Leishmania cause cutaneous and mucocutaneous diseases. Such species are found intracellularly and extracellularly in skin and mucous membranes of humans. Within the genera Trypanosoma, it is well known that certain species reside intracellularly in viscera, mycocardium, and brain in humans. During certain stages of their developmental cycle, these species may also reside in blood, lymph nodes, cerebro-spinal fluid, depending upon whether the organism is residing in the host or the vector.

A particularly preferred haploid genera is Toxoplasma. Toxoplasma is an obligate intracellular parasite. It is well known that Toxoplasma is culturable. All of the known protein-coding genes are present in single-copy. Gene expression in Toxoplasma is apparently conventional; that is, promoters are defined and thematically similar to higher eucaryotes. (See, for example, 1995 *Molecular Approaches to Parasitology*, pp. 211–225, Boothroyd et al. (eds. J. C. Boothroyd & R. Komuniecki; J. Wiley & Sons, N.Y.).) An especially preferred species that is well-characterized is *T. gondii*. Toxoplasma is distributed world-wide and resides in various cells, tissues and fluids of the host. During certain stages, the organism can be found in the central nervous system, skeletal and cardiac muscles, and visceral organs and tissues. Domestic cats are important reservoirs for human infection of this organism. For example, human infection can be transmitted in a variety of ways: handling infected cat feces; ingestion of meat from infected animals such as pork and lamb; transplacental transmission; transfusion with infected blood; and, via organ transplantation from infected donors. Of particular interest herein is the fact that toxoplasmic encephalitis is the most common opportunistic parasitic infection of the central nervous system in patients with AIDS.

As already stated, two particularly preferred genera of protozoa include Leishmania and Toxoplasma. Another currently preferred genera is Giardia. In certain embodiments, other pathogenic amoebae are contemplated. Specifically, the currently preferred unicellular diploid organisms include, but are not limited to: Protozoans of the family Trypanosomatidae (Trypanosomoa cruzi, *T. brucei*, Leishmania spp (including subgenus Leishmania and Viannia; examples include *L. major, L. tropica, L. aeithiopica, L. entrietti, L. mexicana, L. amazonesis, L. donovani, L. chagasi, L. infantum, L. braziliensis, L. panamaensis, L. guyanensis*, and others). The currently preferred haploid organisms include, but are not limited to: members of Apicomplexa (*Toxoplasma gondii*, Plasmodium, Eimeria, Cryptosporidia, and others). Protozoans of uncertain ploidy include, but are not limited to: amoebae including Entamoeba spp, Acanthamoeba spp, Naegleria spp, Giardia lamblia, and members of the phyla including Microspordia and the trichomonads (*Trichomonas vaginalis, Tritrichomonas foetus*).

Other suitable protozoans known to have human hosts include: *Entamoeba histolytica, Entamoeba hartmanni, Entamoeba coli, Entamoeba polecki, Endolimax nana, Iodamoeba buetschlii, Naegleria fowleri, Acanthamoeba species, Dientamoeba fragilis, Giardia lamblia, Chilomastix mesnili, Trichomonas vaginalis, Pentatrichomonas hominis, Enteromonas hominis, Balantidium coli, Blastocystis hominis, Isospora belli, Sarcocystis species, Cryptosporidium parvum, Enterocytozoon bieneusi, Toxoplasma gondii, Plasmodium vivax, Plasmodium falciparum, Plasmodium malariae, Plasmodium ovale, Plasmodium species, Babesia microti, B. equi, B. bigemina, Trypanosoma b. gambiense, T. b. rhodesiense, T. cruzi, T. rangeli, Leishmania species* and *Pneumocystis carinii*.

In view of the present disclosure, the skilled artisan will appreciate that the sustained delivery device exemplified herein is particularly suitable for tissue-targeted applications. Each of the above-described organisms has a tissue preference and each can be exploited by judicious practice and/or routine adaption of the present invention. Tissue-specificity is further discussed in Example 9.

One particularly preferred feature and advantage of the organisms contemplated herein is an ability to escape from the host immune response. The particular mechanism by which this immune evasion is accomplished is not relevant or critical to practice of the present invention. All that is required is that the particular organism be successful, at least in part, in its efforts to invade and reside in the host. The skilled artisan will appreciate that persistence in the host can be, in part, controlled by selection of the particular organism administered to the host. That is, the organisms contemplated herein collectively demonstrate a broad spectrum of persistence in the host. Practice of the present invention permits discrete modification of a particular organism which already has an ability to live and persist in, even if for a limited time, the host body such that it can deliver therapeutic genes/proteins. The above-described organisms have developed this preferred ability to inhabit their host's body. In certain preferred embodiments, the method of making the delivery device described herein can permit controlling or modifying the virulent properties of a particular organism which, in part, permit it to invade its preferred host. In so doing, any of the above-described pathogenic-type organisms can be rendered partially or wholly avirulent as well as conditionally defective. In essence, practice of the present invention results in production and exploitation of "domesticated" protozoa or protozoa parasites.

Evidence that the above-described organisms can be genetically modified using routine methods can be derived from the numerous publications describing protocols, reagents, and other experimental parameters useful therefor. (For example, see 1993 *Protocols in Molecular Parasitology*, ed. J. E. Hyde; Humana Press, Inc., New Jersey; and 1995 *Molecular Approaches to Parasitology*, eds. J. C. Boothroyd & R. Komuniecki; John Wiley & Sons, Inc., New York, the disclosures of both of which are herein incorporated by reference.) Some of the genera routinely studied using art-recognized genetic and molecular techniques include, but are not confined to, Trypanasoma, Leishmania,. Plasmodium, Schistosoma, Giardia, Theileria, and Toxoplasma. In view of the widely publicized materials and methods for genetically modifying organisms such as those described above, it will be appreciated that merely routine experimentation and routine skill is required to practice this present invention with a particular haploid/diploid unicellular organism, including protozoan and/or parasitic organisms.

It is understood that the present invention can be used for applications in which the host is a metazoan organism. That is, a multi-cellular organism including plants and insects as well as mammals is a suitable host. In such applications, the particular organism which serves as the sustained delivery device is one capable of establishing itself in such a host. Examples of such organisms have been described elsewhere herein. Accordingly, the methods of sustained delivery of a conditionally defective organism described herein are not limited to methods of delivering such an organism to a mammal. A mammal is simply an example of a multi-cellular, metazoan organism with which the present invention can be practiced. Thus, in its broadest respects, the present invention features devices and methods of making and using the same for sustained delivery of a therapeutically significant gene/expression product to a metazoan organism, preferably mammals, plants, and insects, and most preferably mammals. Currently, two particularly preferred mammals include humans and primates.

Additionally, the present invention contemplates that the recipient of the disclosed device includes all vertebrates, for example, mammals, including domestic animals and humans, various species of birds, including domestic birds, particularly those of commercial importance. In addition, mollusks and certain other invertebrates have a primitive immune system and are included as a recipient. As used herein, a vertebrate is any member of the subphylum Vertebrata that includes fishes, amphibians, reptiles, birds, and mammals, all of which are characterized by a segmented bone and cartilaginous spinal column. All vertebrates have a functional immune system and respond physiologically by evidencing immunostimulation. An invertebrate is any member of the animal kingdom excluding the vertebrates. Such animals have no back bone or spinal column. Classification includes all animals except fishes, amphibians, reptiles, birds and mammals. Exemplary of such invertebrates are shellfish and mollusks and other related animals. Although the use of immunostimulating agents and delivery of heterologous genes/expression products to invertebrate animals has heretofore not been well documented, one skilled in the art will recognize the applicability of the subject invention to said invertebrates.

Thus, the present invention also provides a method for exploiting protozoa as delivery vehicles for use in insects. It is anticipated that the methods and devices of the present invention will involve preparing conditionally defective diploid organisms, such as protozoa ordinarily stably associated with a particular insect species. In this regard, the present methods and devices can be used to introduce genes corresponding to antibiotics, for example, which have highly selective anti-insecticidal activity. Still another preferred embodiment provides a device for use in plants. For example, it is anticipated that the methods and devices of the present invention can be used to introduce anti-herbicidal and anti-insecticidal activities.

Practice of the invention will be still more fully understood from the following examples, which are presented herein for illustration only and should not be construed as limiting the invention in any way.

EXAMPLE 1

Materials and Methods

The following description exemplifies the materials and methods used to manipulate currently preferred organisms. The following nomenclature is used: DHFR-TS refers to the Dihydrofolate Reductase-Thymidylate Synthase protein, dhfr-ts⁻ refers to a mutant and/or defective gene.

Cell lines, culture, and transfection. All cell lines studied were derivatives of the *L. major* clonal line CC-1 (Kapler, G. M., C. M. Coburn, and S. M. Beverley (1990) *Mol. Cell Biol.* 10:1084–1094). CC-1 is diploid and homozygous at DHFR-TS(+/+); clone E8-5C7 has a heterozygous replacement of the DHFR-TS gene with a hygromycin B resistance marker (+/HYG), and E10-5A3 is a clonal dhfr-ts⁻ knockout that is heterozygous for replacements of DHFR-TS with a G418 resistance marker (NEO) and HYG (NEO/HYG) (Cruz, A., C. M. Coburn, and S. M. Beverley (1991) *Proc. Natl. Acad. Sci. USA* 88:7170–7174, incorporated herein by reference). Promastigotes were cultivated in M199 medium containing 10% heat-inactivated fetal bovine serum (Kapler, G. M., C. M. Coburn, and S. M. Beverley (1990) *Mol. Cell Biol.*

10:1084–1094, incorporated herein by reference) or, for tests for thymidine prototrophy, in a completely defined M199 medium lacking thymidine and supplemented with 0.66% bovine serum albumin (Cohn fraction V), folate, 1.5 $\mu$g of biopterin per ml, 100 $\mu$M adenine, 10 $\mu$g of heme per ml, 40 mM N-2-hydroxyethylpiperazine-N'-2-ethanesulfonic acid (HEPES; pH 7.4), 50 U of penicillin per ml, 50 $\mu$g of streptomycin per ml, and 1 $\mu$g of biotin per ml. As indicated, liquid medium contained G418 (8 $\mu$g/ml), hygromycin B (16 $\mu$g/ml), or thymidine (10 $\mu$g/ml). Cells were enumerated with a Coulter Counter (model Zf). The concentration of MTX required to inhibit cell growth by 50% was termed the $EC^{50}$. Log-phase promastigotes were transfected by electroporation, and colonies were obtained by plating cells on semisolid M199 medium. In MTX selections, colonies appeared after 8–20 days. As indicated, the plates were supplemented with G418 (16 $\mu$g/ml), hygromycin B (32 $\mu$g/ml), thymidine (TdR; 10 $\mu$g/ml), or methotrexate (MTX; 100 $\mu$M). The plating efficiency was determined in parallel on medium containing only hygromycin B and TdR.

DNA manipulations. Leishmania genomic DNA was prepared by the Triton-LiCl miniprep method and used for Southern blot analysis as described in Ellenberger, T. E., and S. M. Beverley (1989) J. Biol. Chem. 264:15094–15103, incorporated herein by reference. Cell slot blots were made as follows. Aliquots (0.1 ml) of stationary-phase cultures were applied to nylon membranes (GeneScreen Plus), prewetted with 2×SSPE (1×SSPE is 0.15 M NaCl, 10 mM $NaH_2PO_2$, and 1 mM EDTA), with a slot blotter apparatus (Schleicher & Schuell). The cells were lysed by treatment in 0.4 N NaOH-1.5 M NaCl for 10 min and then neutralized in 0.5 M Tris HCl (pH 7.5)-3 M NaCl for 10 min. The DNAs were immobilized by baking, and hybridization was carried out as for the Southern blots. Final washes were performed at 67° C. in 0.1×SSPE-0.5% sodium dodecyl sulfate. The DHFR-TS coding-region probe fragment was generated by PCR with genomic DNA as a template. The HYG gene probe was a 1.05-kb BamHI-SpeI fragment from pX63HYG (Cruz, A., C. M. Coburn, and S. M. Beverley (1991) Proc. Natl. Acad. Sci. USA 88:7170–7174). The DHFR-TS locus "near flanking" probe was a 2.0-kb EcoRI fragment from pK300 (Kapler, G. M., C. M. Coburn, and S. M. Beverley (1990) Mol. Cell Biol. 10:1084–1094, the disclosure of which is herein incorporated by reference), and the "far flanking" probe was a 5.7-kb KpnI fragment from plasmid pLTS-D4AJ11-K57. The Leishmania actin probe was a 1.7-kb SalI fragment derived from genomic DNA subcloned in pBluescript. All DNA probes were labeled with $[\alpha^{32}P]$ dCTP by the random-primer method (Felsberg, A. P., and B. Vogelstein (1983) Anal. Biochem. 132:6–13).

Enzyme and transport assays. Crude extracts were prepared by sonication of cells in phosphate-buffered saline (137 mM NaCl, 15 mM KCl, 10 mM $Na_2HPO_4$, 32.6 mM $KH_2PO_4$) containing 1 mM EDTA, 100 $\mu$M phenylmethylsulfonyl fluoride, 150 $\mu$g of benzamidine per ml, 20 $\mu$g of leupeptin per ml, 200 $\mu$g of 110-phenanthroline per ml, and 50 $\mu$g of soybean trypsin inhibitor per ml. Extracts were centrifuged at 13,000×g for 20 to 30 min at 4° C., and the supernatants were taken for enzyme assay, DHFR activity was measured with $[C^3H]H_2$-folate (Moravek Biochemicals) and NADPH using methods known in the art. The concentration of MTX required-to inhibit DHFR activity by 50% was termed the $IC_{50}$. TS activity was measured by the transfer of tritium from 5-$[^3H]$dUMP (Moravek Biochemicals) to $H_2O$ using methods known in the art. $[^3H]$MTX (5 $\mu$M; Moravek Biochemicals) uptake was measured following centrifugation through oil (Ellenberger, T. E., and S. M. Beverley (1987) J. Biol. Chem. 262:10053–10058, incorporated herein by reference). Total soluble protein was determined by the dye-binding methods known in the art. Pteridine reductase 1 (PTR1) protein levels were determined by Western blot (Immunoblot) analysis (Harlow, E., and D. Lane (1988)

Antibodies: A laboratory manual Cold Spring Harbor Laboratory, Cold Spring Harbor, N.Y., incorporated herein by reference) with a rabbit polyclonal antiserum.

dhfr-ts⁻ L. major E10-5A3 was derived from L. major CC-1 by two rounds of targeted gene replacement and bears integrated G418 and hygromycin drug-resistance markers replacing the two DHFR-TS alleles. CC-1 is a clone of strain LT252 (MHOM/IR/83/LT252; Kapler et al. (1990), 10 Mol. Cell. Biol. 1084–1094). Virulent challenge L. major was clone 5 of the LV39 line (Rho/SU/59/P; Marchand et al. (1987), 9 Parasite Immunol. 81–92); it was passed through mice every 4 weeks to maintain virulence. When propagated for immunization or challenges, Leishmania were grown on biphasic NNN medium (Titus et al. (1991), 21 Eur. J. Immunol.559–567; thymidine at 10 $\mu$g/ml was added for dhfr-ts⁻). Metacyclic dhfr-ts⁻ promastigotes were purified by using peanut agglutinin (Sacks, D. L. & Perkins, P. V. (1984) Science 223, 1417–1419) and a freeze-thaw lysate was made (Titus, R. G., Muller, I., Kimsey, P., Cerny, A., Behin, R. Zinkernagel, R. & Louis, J. (1991) Eur. J. Immunol. 21, 559–567). BALB/c and BALB/c athymic nu/nu mice were obtained from the National Cancer Institute (Frederick, Md.); CBA/T6 mice were obtained from The Jackson Laboratory. Subcutaneous injections (s.c.) were delivered at a shallow site in the hind footpad, i.v. inoculations were into the tail vein, and i.m. injections were into the large rear leg muscle mass. Lesion progression was followed by using a vernier caliper (Titus, R. G., Muller, I., Kimsey, P., Cerny, A., Behin, R. Zinkernagel, R. & Louis, J. (1991) Eur. J. Immunol. 21, 559–567). Macrophages were elicited with starch in the peritoneum of BALB/c mice, harvested, and infected with parasites, and their parasite burden was assessed as described (Titus, R. G., Kelso, A., & Louis, J. A. (1984) Clin. Exp. Immunol. 55, 157–165). The limiting dilution assay for enumerating parasites in infected mouse tissues was performed as described (Titus, R. G., Marchand, M., Boon, T. & Louis, J. A. (1985) Parasite Immunol. 7, 545–555). Lymph node cell proliferation assays were performed as described (Kimsey, P. B., Theodos, C. M., Mitchen, T. K., Turco, S. J. Titus, R. G. (1993) Infect. Immun. 61, 5205–5213). Osmotic pumps (14-day Alzet model 2002; Alza) were loaded with thymidine at 42 mg/ml and implanted 1 day prior to infection with dhfr-ts⁻.

A method for constructing dhfr-ts⁻ L. major strains using null-targeting methods of the invention is described in Example 2. The disclosures of the above-cited references are incorporated herein by reference.

EXAMPLE 2

Method for Producing Conditionally Defective Mutants Excision Technologies

The following non-limiting example illustrates one embodiment of the present methods for null-targeting deletion of the exemplary DHFR-TS locus in a currently preferred organism.

A. A protocol for null targeting of diploid cells was developed, in which transfection of a DHFR-TS deletion construct into Leishmania cells followed by negative selection yielded parasites lacking exemplary DHFR-TS or foreign sequences.

Negative DHFR-TS selection was used in a protocol termed null-targeting, which simultaneously deletes both copies of the chromosomal DHFR-TS gene without inserting any selectable marker. This approach, which can be applied to other diploid organisms, was used here to generate a marker-free dhfr-ts⁻ mutant parasite (Titus. R. G., F. J. Guelros-Filbo, L. A. R DeFreitas, and S. M. Beverley (1995) *Proc. Natl. Acad. Sci. USA* 92:10267–10271, incorporated herein by reference). In *L. major*, as in all protozoan and plant species known, the genes encoding dihydrofolate reductase (DHFR) and thymidylate synthase (TS) have been joined to generate a bifunctional fusion protein (Beverley, S. M., T. E. Ellenberger, and J. S. Cordingley (1986) *Proc. Natl. Acad. Sci. USA* 3:2584–2588; Lazar, G., H. Zhang, and H. M. Goodman (1993) *Plant J.* 3:657–668, the disclosures of which are incorporated herein by reference.). It is possible to select against the activity of the DHFR-TS protein by plating parasites in the presence of methotrexate plus thymidine (MTX+TdR). Since DHFR-TS activity can be selected for in the absence of exogenous TdR (Cruz, A., and S. M. Beverley (1990) *Nature* (London) 348:171–174, incorporated herein by reference), DHFR-TS thus may be used as a positive-negative marker in *L. major*.

Selection against DHFR-TS in *L. major*. In prokaryotes, loss of TS activity confers transient resistance to antifolates if thymidine is provided (Bertino, J. B. and K. A. Stacey (1966) *Biochem J.* 101:32C-33C; Stacey, K. A. and E. Simson (1965) *J. Bacteriol.* 90:554–555). This stems from a sparing of reduced-folate pools, since TS is the only significant enzyme whose activity oxidizes tetrahydrofolates. It was predicted that the absence of the bifunctional DHFR-TS would confer a similar if not stronger phenotype in Leishmania spp. as a result of linkage of the two enzymatic activities. This was tested with a panel of cells, obtained by homologous gene replacement, which contained either one (+/HYG) or no (NEO/HYG) copies of DHFR-TS. In liquid media, wild-type or heterozygous cells show typical sensitivities to MTX ($EC_{50}$, about 1 $\mu$M), while the dhfr-ts⁻NEO/HYG knockout grew well at 100 $\mu$M MTX. Permanent MTX resistance may arise from the provision of reduced folates by the alternate pteridine reductase PTR1 in *L. major*.

These data suggested that MTX+TdR could be used as a selection against Leishmania DHFR-TS. Accordingly, 20×10⁶+/HYG Leishmania cells were plated on medium containing MTX-TdR, and colonies appeared at a frequency of 0.7×10⁻⁵ to 2.5×10⁻⁵ per cell plate. In contrast, wild-type cells bearing two copies of DHFR-TS (+/+) did not give rise to any colonies. Omission of TdR also gave no colonies, suggesting that those obtained with TdR did not arise from common MTX resistance mechanisms, such as amplification of DHFR-TS or PTR1, mutations in DHFR, or from altered MTX accumulation, as described previously for numerous Leishmania lines and species (Arrebola, R., A. Olmo, P. Reche, E. P. Garvey, D. V. Santi, L. M. Rulz-Parez, and D. Gonzalez-Pacanowska (1994) *J. Biol, Chem.* 269:10590–10596; Beverley, S. M. (1991) *Annu. Rev. Micro-biol.* 45:417–466; Borst, P. and M. Ouellette (1995) *Annu. Rev. Microbiol.* 49:427460; Ellenberger, T. E. and S. M. Beverley (1987) *J. Biol. Chem.* 262:13501–13506).

DHFR-TS as a negative marker in primary transfections. To test the use of selection against DHFR-TS in primary transfection experiments, a 7.8-kb BglII targeting fragment derived from plasmid pR, which contains a deletion of the whole DHFR-TS coding region (Kapler, G. M., C. M. Coburn, and S. M. Beverley (1990) *Mol. Cell Biol.* 10:1084–1094, the disclosure of which is herein incorporated by reference) was used. Homologous replacement at DHFR-TS by this fragment was expected to yield a deletion of the gene. To exhibit the desired dhfr-ts⁻ phenotype following transfection of diploid wild-type cells, two events were required, either two independent replacements or one replacement combined with LOH.

Ten micrograms of the purified targeting fragment or an equimolar amount of BglII digested pR was electroporated into wild-type *L. major*, and the cells were plated on MTX+TdR Seven colonies were obtained in the transfected cells, four of which were thy⁻. In contrast, two colonies were obtained in mock-transfected controls, both of which were thy⁺. All five thy⁺ colonies were noticeably smaller than the thy colonies, and it was presumed that they represent the expected background of events involving known MTX resistance mechanisms, structural alterations of TS, or breakthroughs. In contrast, cell and Southern blot analysis of the four thy⁻ colonies showed that three contained the planned homozygous deletion. Hybridization with a DHFR-TS probe confirmed the loss of DHFR-TS. The fourth contained one deletion allele plus another bearing a more complex event which also resulted in deletion of DHFR-TS. Similar complex events have been described previously at DHFR-TS in cells transfected with large amounts of targeting fragment (Cruz, A., and S. M. Beverley (1990) *Nature* (London) 348:171–174). These data demonstrate the ability to perform direct selection against DHFR-TS in diploid wild-type *L. major*.

Null-targeting strategies as a general tool. Using the negative DHFR-TS selection and transfection of a null-targeting fragment, it was possible in one step to generate Leishmania spp. deleted for both copies of DHFR-TS. This null-targeting approach could be applied at any locus for which an appropriate negative selection can be devised, without sacrificing any selectable marker. A large number of loci are potentially suitable targets for this purpose in different species, including TK, the orotidine 5'-phosphate-decarboxylase locus, HGPRT, APRT, TS, or DHFR-TS. This protocol could also be used to introduce any given coding region directly into the genome, by construction of a null targeting fragment in which the negative selectable gene (DHFR-TS here) was replaced with another coding region. This would be advantageous in many circumstances and these approaches can be applied to cells from any diploid species. The null-targeting methods disclosed herein can also be used to delete a single allele or copy of a given genetic locus in a diploid, by applying appropriate intermediate levels of negative selection to select against only one of the alleles or genetic loci. The resulting colonies can be screened for the presence of both a wild-type copy and a deleted copy of the allele or genetic locus, using Southern blot analysis methods known in the art.

B. Selection against DHFR-TS on a heterozygous line (+/HYG) was used to generate colonies exhibiting both loss of heterozygosity (LOH) and structural mutations in DHFR-TS, permitting the first measurement of mutation frequencies in this parasite. Loss of heterozygosity occurred at a frequency ranging from 10⁻⁴ to 10⁻⁶ and was elevated 24-fold by treatment with $\gamma$-irradiation, while the frequency of other events was less than 10⁻⁶ and was increased more than 1,000-fold by nitrosoguanidine treatment. The frequency of loss of heterozygosity relative to other processes such as mutation and gene replacement has important implications for genetic variability in natural Leishmania populations and the generation of both targeted and random mutations.

Cell blot hybridizations were performed to determine whether the colonies obtained by selection against DHFR-TS on the +/HYG line contained DHFR-TS sequences. The colonies that lacked DHFR-TS sequences are referred to as DTSΔ, whereas the colonies that retained the gene in some form are referred to as DTS+.

DTSΔ lines have undergone a LOH event. Southern blot hybridization was used to probe the structure of the DHFR-TS locus in the DTSΔ lines. A DHFR-TS coding-region probe confirmed the absence of DHFR-TS. A flanking probe showed no alterations in the structure of either the DHFR-TS or HYG replacement alleles, other than loss of the DHFR-TS allele in the DTSΔ lines. A wild-type structure was also found in Southern blots with a probe encompassing 30 kb of DNA spanning DHFR-TS. Moreover, no changes in the size of the 500-kb DHFR-TS chromosome could be detected in contour-clamped homogeneous electric field gel electrophoresis blots hybridized with a probe located 100 kb 5' of DHFR-TS. Thus, the DTS+ and DTSΔ lines have not undergone deletion or DNA rearrangements.

The HYG copy number in several DTS+ and DTSΔ lines was measured in Southern blot and slot blot analysis, using hybridization with a Leishmania actin probe to control for DNA loading. Assuming the HYG copy number in the parent +/HYG to be 1, values approaching 2 were found for the DTSΔ lines (1.7±0.2, 1.7±0.3, 1.6±0.3, and 1.5±0.2 [n=4] for colonies LH1, LOH 5-1, LOH 5-2, and LOH 5-3, respectively) and close to 1 for the DTS+lines (0.7±0.2 and 0.8±0.2 for colonies F22 and PM13, respectively). In combination with the Southern blot data described above, it appeared that the LOH event in the DTSΔ lines did not occur by chromosome loss but arose from an event where loss of the DHFR-TS allele was coupled to duplication of the HYG allele. Potential mechanisms include gene conversion, mitotic crossing over, or some form of chromosome mis-segregation.

Positive selection for LOH. Normally, the +/HYG parasite was propagated in medium lacking TdR and containing 16 μg of hygromycin B per ml. Several independent cultures of this line were serially passaged in medium containing TdR and either 250 or 500 μg of hygromycin B per 1 (for the +/HYG line, 200 μg of hygromycin B per ml results in a 50% reduction in growth). At the higher drug concentrations, a decreased rate of growth was observed initially but the cultures rapidly adapted and grew a near-normal rates thereafter. After 9 to 12 passages (each at a 1:100 dilution, for a total of 60 to 80 cell doublings), the frequency of colony formation on MTX-TdR plates rose dramatically, ranging from 0.001 to 0.95 in different cultures. Both concentrations of hygromycin B worked equally well. Similar results were obtained by selecting the NEO/HYG dhfr-ts$^-$ knockout in an analogous fashion, which yielded a HYG/HYG knockout homozygote.

The rate of increase of colony formation on MTX+TdR plates was measured as a function of the period of growth at higher hygromycin B concentrations. On average, every three passages resulted in about a 10-fold increase in colony formation. Again, no correlation was found between hygromycin B concentration and the frequency of colonies on MTX+TdR plates. The DHFR-TS phenotype in the colonies arising from these studies were not systematically examined, but those tested always belonged to the DTSΔ class. Thus, elevated drug pressure can be used effectively to induce homozygosity from eterozygous replacements in *Leishmania major*.

The system established here has several direct applications. First, the defective DHFR-TS mutants can be used to explore the role of particular amino acids in the activity or stability of this key metabolic protein. Second, the type and frequency of mutations induced by other mutagenic treatments can be characterized, and these data incorporated into improved mutant recovery protocols as outlined above. It would be particularly interesting to examine the effects of oxidative stress on mutagenesis, since the entry of Leishmania cells into, and propagation within, the phagolysosome of the vertebrate macrophage may expose the parasite to this class of DNA-damaging agents as part of the normal infectious cycle. Potentially, measurement of alterations at DHFR-TS within the DHFR-TS/HYG heterozygote can be used as a probe of the exposure of Leishmania spp. to mutagenic stress during the natural infectious cycle.

The occurrence of LOH has important uses in the conservation of genetic markers in transfectional manipulations of the Leishmania genome. The selection of +/HYG DHFR-TS heterozygote with elevated hygromycin B levels rapidly gave rise to thy$^-$ parasites completely lacking DHFR-TS. This permits the use of a single targeting construct and transfection to obtain null mutants for genes for which negative selections are unavailable. Of course, the LOH-based approach can be accelerated by the application of negative selections. Homozygous HYG/HYG replacements at the LPG2 locus of *L. donovani* by lectin selection against lipophosphoglycan expression were generated in this manner (Descoteaux, A. H., et al., (1995) *Science* 269:1869–1873, incorporated herein by reference).

EXAMPLE 3

General Method for Generating Null-Targeted Deletions

This method can be used to generate null-targeted deletions at any non-essential genetic locus by exploiting the fact that DHFR-TS can act both as a positive and a negative marker. In this example, a given non-essential genetic locus is targeted for deletion. Non-essential, as defined herein, means that deletion of the locus is not lethal to the cell. In this example, the use of DHFR-TS as both a positive and a negative marker requires that the cell be dhfr-ts$^-$, and preferably does not contain any DHFR-TS gene sequence so as to avoid homologous recombination with the DHFR-TS sequences. In a first step, the cell is transfected with DNA comprising the DHFR-TS gene flanked by sequences complementary to the sequences flanking the targeted non-essential gene. Positive selection for DHFR-TS isolates cells having undergone homologous recombination to replace the target gene with the DHFR-TS gene. The replacement is confirmed using Southern blotting methods known in the art, and disclosed herein. In a second step, this cell containing the DHFR-TS gene at the desired genetic locus is transfected with DNA comprising the same flanking sequences as above, but with no DNA inserted between the flanking sequences. Negative selection against DHFR-TS, using methods disclosed herein, permits isolation of cells having lost the DHFR-TS gene due to homologous recombination. These cells are now deleted for the non-essential target genetic locus-such that no DNA sequence replaces the target genetic locus. The deletion is confirmed using Southern blotting methods known in the art, and disclosed herein.

One of ordinary skill in the art will understand that this method, combined with the teachings in this disclosure, can be used to generate null-targeted deletions in haploid cells, diploid cells or cells of higher ploidy. In diploid cells, this method can be used to delete one or both alleles of a given non-essential genetic locus. It will be understood by the skilled artisan that this example is illustrative of the use of both positive and negative markers to null target any non-essential gene. The skilled artisan will also understand that the above-described method can also be used to replace any non-essential genetic locus with a gene of interest.

In this example, the DHFR-TS gene acted initially as a positive marker and subsequently as a negative one. However, this method can be used with positive and negative markers that are encoded by different genes. In such a scenario, the DNA that is transfected in step 1 above comprises both the positive and the negative marker genes between the flanking sequences.

EXAMPLE 4

Method for Producing Conditionally Defective Mutants Transposon Technologies To test whether mariner could transpose in Leishmania, two plasmids were constructed: pX63TKNEO-TPASE, containing the transposase gene under the control of leishmanial sequences necessary for its expression, and pX63PAC-Mos1, containing an intact copy of the transposon. The plasmids were sequentially introduced into the *L. major* line +/Δ1, and 22 independent double transfectants were analyzed for mariner transpositions by Southern blot hybridization. Five out of 22 clones showed extra mariner hybridizing bands distinct from the ones corresponding to the input plasmids suggesting the occurrence of transposition. Several of these bands were isolated by inverse PCR, and analysis of their sequences demonstrated that they had the structure expected for true transpositions, with an intact transposon end followed by a TA dinucleotide and a stretch of DNA not present in the donor plasmids. Southern blot experiments using inverse PCR products as probes identified bands in the parental +/Δ1 line that were increased by ~1.3 kb, the expected for a mariner insertion, in the clone that gave rise to the PCR product, providing further evidence that they represent "bona-fide" transposition events and not PCR artifacts. Assuming that all the novel mariner bands detected in this experiment are due to transposition, we conclude that mariner is being mobilized at a very high frequency, in about 20% of the colonies tested.

Tests were performed to determine whether heterologous expression of mariner could produce the insertional inactivation of a Leishmania gene. The DHFR-TS locus was chosen as the target, as it is hemizygous in +/Δ1 and because we can select for its inactivation. Plating of mariner-containing strains on methotrexate (MTX) and thymidine produced dhfr-ts$^-$ mutants at an overall frequency of $1.2 \times 10^{-4}$ and with a distribution of loss of heterozygosity and mutational events. Among the dhfr-ts$^-$ mutants that retained DHFR-TS sequences, one clone, 22M3, showed a larger DHFR-TS allele in Southern blots. The increase in size (~1.3 kb) suggested the insertion of mariner in DHFR-TS and, indeed, rehybridization of the blot with a mariner probe identified a band in 22M3 identical in size to the DHFR-TS band. Sequencing of the insertion in 22M3 confirmed that mariner transposed into DHFR-TS, more precisely, into a TA dinucleotide located at position 532 of the coding region. Interestingly, the insertion of mariner at DHFR-TS led to duplication of the target TA. This result, together with the sequences of the transpositions, which always show a TA flanking the 5' and 3' end of the transposon, suggest that mariner transposition in Leishmania leads to target site duplication and thus occurs by the typical mechanism described for the mariner/Tc1 family. Considering that disruption of DHFR-TS by mariner represented 1/48 of the dhfr-ts$^-$ lines analyzed, we can derive a frequency of $2.5 \times 10^{-6}$ for the insertional inactivation of one allele of a gene in Leishmania. This frequency becomes $\sim 10^{-1}$/genome, if we take into account that DHFR-TS represents about 1/30, 000 of the parasite's nuclear DNA.

A skilled artisan will appreciate that the transposon insertion method described herein can be used to inactivate other genes against which a negative selection can be applied. The mariner transposon element can therefore be used to isolate other conditionally defective mutants. It will be further understood that the methods described herein can be used to generate transposon insertion mutants in other protozoans. The mariner transposon element can be used in, for example, Toxoplasma, Giardia, and Trypanosoma, to create conditionally defective mutants using the methods of the invention.

Next, it was determined whether a modified mariner element carrying a drug resistance marker could be used in a "gain of function" selection for mRNA processing signals in the Leishmania genome. The selectable mariner, named MosHYG, has a hygromycin resistance gene (HYG) inserted next to its 5' end and is cloned in the vector pX63PAC in the anti-sense orientation relative to the Leishmania trans-splicing signals, such that no processed HYG message can be produced. MosHYG has in-frame stop codons upstream of the HYG ATG and therefore should yield only transcriptional fusions. Transfections with pX63PAC-MosHYG produced hundreds of colonies when plated on puromycin and no colonies when plated on hygromycin confirming that HYG is silent in the context of the donor plasmid. However, transposase-expressing lines carrying pX63PAC-MosHYG gave rise to hygromycin-resistant (hyg$^r$) colonies at a frequency ranging from less than $10^{-6}$ to $10^{-3}$ when replated in 32 μg/ml of the drug, suggesting that the element was moving. Activation of HYG due to transposition should produce chimeric MosHYG mRNA's: containing Leishmania sequences preceded by the ubiquitous trypanosomatid spliced leader on the 5' end. We tested this using the well-known RT-PCR and found that MosHYG had indeed transposed to several different Leishmania loci, most of which didn't show any matches in sequence data bases. One of the cDNAs (T1.2D) identified an event that trapped the splice acceptor site and 5' untranslated region of DHFR-TS. This corresponds to a transposition within the donor plasmids which use DHFR-TS flanking sequences to drive the drug markers, and demonstrated that our selection for processing signals was working as expected. Northern analysis using probes derived from the uncharacterized loci identified transcripts in wild type Leishmania that are increased in size the hyg$^r$ clone that originated the RT-PCR product. This confirmed that the chimeric mRNAs are not PCR artifacts and that an engineered mariner can generate gene fusions capable of identifying Leishmania genetic elements.

Additionally, it is understood that the methods described herein can be used to identify genetic elements conferring different levels of expression or under different types of regulatory control. A modified mariner element analogous to MosHYG, but wherein the hygromycin gene is replaced by the Green Fluorescent Protein gene (Ha, Schwartz, Turco, Beverley, *Molec. Biochem. Parasitol.* 77: 57–64, 1996, incorporated herein by reference), can be used to identify these different types of genetic elements. Transposition events are generated using the methods described above. Transposition events that result in Green Fluorescent Protein expression (productive transposition events) can be identified by assaying Green Fluorescent Protein expression using methods known in the art and described in Example 6. Expression of Green Fluorescent Protein in Leishmania can be assayed in culture medium, in cultured macrophages and in vivo. Different productive transposition events will give rise to different levels of Green Fluorescent Protein expression, and to expression under different growth conditions. The genetic elements responsible for these different levels and patterns of expression can be readily identified, using methods known in the art, by studying the sequences flanking the site of insertion of the modified transposon. It is also expected that genetic elements can be identified in other unicellular organisms using the methods described herein, in combination with methods known in the art, and only routine experimentation.

It will be appreciated by the skilled artisan that certain of the above-described organisms, as well as the transfecting DNA sequences used to produce them, can be components of a kit for practice of the present invention. For example, a kit comprising any one of the conditionally defective organisms described in Examples 2, 3 or 4 provides the skilled artisan with the ability to make delivery vehicles expressing a particular therapeutically-significant substance. Additionally, a kit comprising any one of the transfecting or transforming sequences (or a combination thereof) described in Examples 2, 3 or 4 provides the skilled artisan with the compositions required to make conditionally defective organisms for subsequent use as delivery vehicles.

EXAMPLE 5

Method of Sustained Delivery of Expression Product for Immunostimulation

A. Vaccination with live Leishmania major has been shown to yield effective immunization in humans; however, this has been discontinued because of the problems associated with virulence of the available vaccine line. To circumvent this, the ability of a dhfr-ts$^-$ null mutant (E10-5A3) of L. major, obtained by gene targeting, to infect and then to vaccinate mice against challenge with virulent L. major was tested. Survival and replication of dhfr-ts$^-$ in macrophages in vitro were dependent upon thymidine, with parasites differentiating into amastigotes prior to destruction. dhfr-ts$^-$ parasites persisted in BALB/c mice for up to 2 months, declining with a half-life of 2–3 days. Nonetheless, dhfr-ts$^-$ was incapable of causing disease in both susceptible and immmunodeficient (nu/nu) BALB/c mice. Animal infectivity could be partially restored by thymidine supplementation. When inoculated by the i.v., s.c., or i.m. routes into mice, dhfr-ts$^-$ could elicit substantial resistance to a subsequent challenge with virulent L. major. Thus, Leishmania bearing auxotrophic gene knock-outs can be safe and induce protective immunity. As described earlier, such a genetically modified also can be used as a platform for delivery of immunogens relevant to other diseases.

Inability of dhfr-ts$^-$ to Cause Disease in Mice. The ability of dhfr-ts$^-$ to infect BALB/c mice, was tested by innoculating stationary-phase parasites s.c. into one hind foot-pad. Stationary-phase organisms were used as this provides the infective metacyclic stage of L. major (typically 5% for dhfr-ts$^-$).

E10-5A3 dhfr-ts$^-$ was derived from the CC-1 line of L. major, which is less infective than virulent VL39 clone 5 and requires ≈10-fold more inoculating parasites to give a similarly rapid progression of disease. Large numbers ($10^8$ cells per mouse) of dhfr-ts$^-$ did not induce cutaneous lesions, even after 2.5 years. In contrast, $10^7$ virulent LV39 or $10^8$ parental CC-1 parasites gave severe disease, with lesions that progressed rapidly and at similar rates. Inoculation of only $10^6$ CC-1 parasites yielded lesions after a delay of a90 days.

Vaccinating BALB/c Mice with dhfr-ts$^-$ i. v. Induces Substantial Immunity to Virulent L. major. While the dhfr-ts$^-$ line can persist in mice, it does not cause disease. To test its ability to induce protective immunity, BALB/c mice were vaccinated with stationary-phase dhfr-ts$^-$ and challenged 1 week later with $10^6$ virulent L. major, delivered s.c. Vaccination i.v. induced high levels of immunity, consistent with previous studies showing this to be the most effective route to induce immunity against L. major in mice (Liew, F. Y. (1989) in *Vaccination Strategies of Tropical Diseases*, ed. Liew, F. Y. (CRC, Boca Raton, Fla.), pp. 239–253, incorporated herein by reference). The most striking results were achieved with intermediate doses of dhfr-ts$^-$ ($10^5$–$10^6$ parasites). For example, animals vaccinated with $10^5$ dhfr-ts$^-$ controlled lesion development for 277 days. The basis for the dose dependency has not yet been studied further but is interesting in light of the results of Bretscher et al. (Bretscher, P. A., Wei, G., Menon, J. N. & Bielefeldt-Ohmann, H. (1992) *Science* 257, 539–542) who showed that administrating low doses of virulent L. major conferred protection to BALB/c and CBA mice.

With BALB/c mice, vaccination with purified metacyclic dhfr-ts$^-$ was as effective as stationary-phase dhfr-ts$^-$. A metacyclic dhfr-ts$^-$ lysate did not confer protection, other workers have also reported that parasite lysates are ineffective. Similar results were obtained when mice were challenged 1 month after vaccination. Vaccination by the s.c. route imparted minimal protection.

There was a correlation between lesion size and parasite burden in vaccinated BALB/c mice. In mice vaccinated with stationary-phase dhfr-ts$^-$, the parasite burden was reduced 158-fold at day 34 and 1900-fold at day 62 of infection.

Vaccinating CBA Mice with dhfr-ts$^-$ i.v., s.c. or i.m. Induces Substantial Immunity. Resistant CBA mice were vaccinated with dhfr-ts$^-$, as the disease progression in this strain more closely resembles that observed in human infections. In these experiments, mice were vaccinated with stationary-phase dhfr-ts$^-$ and challenged with virulent L. major after 1 week. Similar results were obtained after vaccination with purified metacyclics and challenge after 1 month.

Like BALB/c mice, i.v. vaccination of CBA mice with dhfr-ts$^-$ was highly protective. Unlike BALB/c mice, CBA mice were protected best by large doses of dhfr-ts$^-$ ($10^8$). Significantly, vaccination of CBA mice with $10^8$ dhfr-ts$^-$ by either the s.c. or i.m. routes was protective, although less so that by the i.v. route. Lower doses of dhfr-ts$^-$ induced less protection by the s.c. or i.m. routes. The parasite burden was decreased in all vaccinated animals, as much as 22-fold in mice vaccinated by the i.v. route and 16-fold by the s.c. route.

To test the specificity of the immune response to dhfr-ts$^-$, draining lymph node cells were recovered 1 week after s.c. vaccination of CBA mice with $10^8$ dhfr-ts$^-$ and tested for stimulation by several antigen preparations. Neither bacillus Calmette-Guerin (5×$10^5$ cells per ml) nor ovalbumin (250 µg/ml) induced proliferation as measured by [$^3$H] thymidine incorporation (1100±1000 cpm or 2600±1100 cpm, respectively), while LV39 L. major (5×$10^5$ cells per ml) induced vigorous proliferation (116,000±9000 cpm).

Importantly, the dhfr-ts$^-$ organism can be regulated such that it is unable to establish a permanent infection or cause disease in the most susceptible strains of mice tested, relative to the wild-type organism. This arises from the lack of DHFR-TS, as shown by rescue of dhfr-ts$^-$ both in vitro and in vivo by thymidine supplementation, and described in Example 7. The levels of thymidine available within the parasitophorous vacuole appear insufficient to permit propagation and pathogenesis. Even artificial continuous administration of massive subtoxic thymidine supplementation was only able to partially restore infectivity to dhfr-ts$^-$, and lesions immediately regressed upon thymidine withdrawal. Given the tight physiological regulation of thymidine levels (Tattersall, M. H., Brown, B. & Frei, E., III (1975) *Nature* (London) 253, 198–200), it is unlikely that rescue of this particular conditionally effective organism could occur during natural infections.

Despite the block to propagation and pathogenesis, the low thymidine levels available to Leishmania in vivo are apparently sufficient to prevent or delay classic rapid thymine-less death. This follows because dhfr-ts$^-$ did not perish immediately in vivo but, instead, slowly declined over a period of months. Complete removal of thymidine results in rapid death within a few days in vitro (Cruz, A. & Beverley, S. M. (1990) *Nature* (London) 348, 171–174, the disclosure of which is herein incorporated by reference). Thus, subtle interactions between dhfr-ts$^-$ and the host exist that promote limited persistence simultaneously with differentiation. Minimally, this should prolong the period of exposure to both live and dead parasite antigens, while differentiation of dhfr-ts$^-$ would deliver substantial quantities of amastigote antigens. These features are advantageous to vaccination efforts and may perhaps be unique to dhfr-ts$^-$ knockouts, relative to other potential candidate attenuating loci that we have considered.

B. Marker-free dhfr-ts$^-$ Leishmania knockouts as attenuated live vaccine line. In many situations, the introduction of selectable markers may not always be desirable, as in organisms destined for certain uses outside the laboratory. For example, it was shown previously that dhfr-ts$^-$ parasites containing marker genes have potential as live, attenuated vaccines against cutaneous leishmaniasis in a susceptible mouse model (Titus. R. G., F. J. Guelros-Filbo, L. A. R. DeFreitas, and S. M. Beverley (1995) *Proc. Natl. Acad Sci USA* 92:10267–10271, the disclosure of which is herein incorporated by reference). The NEO resistance marker present in this line can inactivate the aminoglycoside paromomycin, which shows some efficacy in antileishmanial chemotherapy (Gueiros-Filbo, F. J. and S. M. Beverley (1994) *Exp. Parasitol.* 78:425–428, the disclosure of which is herein incorporated by reference). It is possible that NEO genes from auxotrophic vaccine lines could find their way into natural field populations, thereby possibly compromising paromomycin therapy. The use of marker-free knockouts as described herein above in Examples 2 and 3 circumvents this problem, because they lack any selectable marker gene coding sequences. Data are available from tests in murine models which indicate that the efficacy of a marker-free mutant as a live vaccine is uncompromised and comparable to that of the previously studied marker-containing (NEO/HYG) dhfr-ts$^-$ null mutant. Moreover, data are available in non-human primate models which indicate that the dhfr-ts$^-$ parasite does not cause any pathology in this system as well.

EXAMPLE 6

Method for Sustained Delivery of a Heterologous Expression Product

The organisms embodied in Example 5 also illustrates the sustained delivery of a heterologous expression product by a device comprising such organisms. In that Example, the expression product is a heterologous drug resistant marker, i.e. an enzyme expressed by a heterologous gene which renders the organism drug-resistant. It is expected that other expression products can be delivered by a device comprising appropriately modified organisms as taught herein.

As a further example, it has been shown (LeBowitz, Coburn, McMahon-Pratt and Beverley, PNAS 87:9736–9740 1990, incorporated herein by reference) that Leishmania promastigotes, transfected with the expression vector pX containing an inserted β-galactosidase gene, contain nearly 1% of their total cellular protein as β-galactosidase. Infective parasites containing this same construct were prepared and β-galactosidase levels determined in promastigotes and amastigotes (infective macrophage stage of Leishmania) recovered from lesions of infected mice. Relative to promastigotes, amastigotes synthesized about 10% as much β-galactosidase, which would correspond to about 0.1% of total cellular protein. Similar experiments carried out with a newer expression vector, pXG (Ha, Schwarz, Turco, Beverley, *Molec. Biochem. Parasitol.* 77:57–64 1996, incorporated herein by reference) show that relative to promastigotes, amastigotes synthesized about 50% as much β-galactosidase. Similar experiments can be carried out using Green Fluorescent Protein instead of β-galactosidase. Green Fluorescent Protein can be effectively expressed in Leishmania, and its expression can be monitored by fluorescence. These data confirm the ability to create genetically modified parasites synthesizing high levels of a foreign, heterologous protein in the desired parasite stage infecting the host.

EXAMPLE 7

Method of Regulating Growth and/or Persistence By Providing/Depriving Host of Agent Required Therefor Inability of dhfr-ts$^-$ to Replicate in Macrophages in Vitro. dhfr-ts$^-$ *L. major* is auxotrophic for thymidine as the free-living promastigote form in vitro (Cruz, A. & Beverley, S. M. (1990) *Nature* (London) 348,171–174; Cruz, A., Coburn, C. M. & Beverley, S. M. (1991) *Proc. Natl. Acad. Sci. USA* 88, 7170–7174).

Starch-elicited peritoneal macrophages were infected in vitro with virulent Leishmania (LV39 clone 5) or dhfr-ts$^-$. Both lines were taken up by the macrophages. Beyond 24 hr, virulent Leishmania continued to replicate as amastigotes within the macrophages. In contrast, dhfr-ts$^-$ did not replicate. Significantly, after 24 or 48 hr, dhfr-ts$^-$ within macrophages appeared morphologically as amastigotes, even in the absence of thymidine. To confirm that the disablement of dhfr-ts$^-$ arose specifically from the lack of DHFR-TS, we added thymidine (100 μg/ml) to the medium, which restored both survival and replication.

In several experiments, attempts were made to rescue the dhfr-ts$^-$ phenotype in vivo, by implanting osmotic pumps that delivered thymidine at the maximum tolerated dose for either 14 or 28 days. Small lesions (up to 0.25 mm) were obtained after infection with $10^8$ dhfr-ts$^-$. The small size, relative to infection with CC-1, may be due to (i) the rapid clearance of thymidine the bloodstream, (ii) deliver of insufficient thymidine to the Leishmania phagolysosomal compartment, and/or (iii) a need in vivo but not in vitro for reduced folates, beyond the capacity of the alternative pteridine reductase PTR1. Significantly, upon removal of the thymidine pumps, dhfr-ts$^-$ lesions regressed immediately and disappeared within 2 weeks.

Finally, the ability of dhfr-ts⁻ to induce cutaneous lesions in BALB/c athymic nu/nu mice, which are severely immunocompromised and the most permissive host known for *L. major*, was tested. Cutaneous lesions did not occur for 220 days after infection with $10^8$ dhfr-ts⁻, the maximum observation period since nu/nu mice die prematurely.

The studies above addressed infectivity by the criterion of visible lesion development. Since Leishmania can persist in the absence of overt disease, the number of viable dhfr-ts⁻ parasites was measured after infection. Susceptible BALB/c mice were injected s.c. in one hind footpad with $10^8$ dhfr-ts⁻. Parasites and, at various intervals, were sacrificed, and parasites were enumerated in the footpad and the draining lymph node. The dhfr-ts⁻ parasites persisted for approximately 2 months, although their numbers declined with a half-life of 2–3 days. From the macrophage results, we infer that the persisting parasites were amastigotes.

EXAMPLE 8

Other Sustained Delivery Vehicles, and Methods of Making and Using the Same

It is expected that the methods of the invention can be used with all unicellular protozoan organisms, particularly parasitic protozoa irrespective of their ploidy, to generate sustained delivery devices. The following non-limiting examples illustrate three currently preferred organisms which could be modified to generate sustained delivery devices.

Toxoplasma is an exemplary haploid parasitic protozoa. The skilled artisan will understand that the method of the invention can be used to render Toxoplasma conditionally defective and capable of expressing a gene product of interest. Since Toxoplasma is haploid, only one allele at any given genetic locus is deleted using the null-targeting method of the invention. Toxoplasma is useful for immunostimulation, because it stimulates very good CDS/MHC class I responses. Toxoplasma is also particularly well-suited for drug delivery to humans since a significant fraction of the population already harbors some form of Toxoplasma.

Trypanosoma and Giardia, protozoa that are, respectively, diploid and of unknown ploidy, are other exemplary organisms that can be used as sustained delivery devices according to the methods of the invention. Giardia could be used to stimulate mucasal immunity. As described herein, the methods of the invention can be used to null-target one, several or all alleles of a given genetic locus in a polyploid organism. The advantages of using different delivery devices to target substances to different tissues within a host organism will become apparent from the teachings provided herein (Example 9).

EXAMPLE 9

Prospective Applications of Sustained Delivery Vehicles

As disclosed above, the present invention can be used to prepare devices for sustained delivery of numerous therapeutically-significant substances and treatment of a variety of clinical indications. The following non-limiting examples are illustrative of such devices and methods of treatment.

Lysosomal Storage Diseases

It is anticipated that the present invention will permit treatment and/or amelioration of lysosomal storage diseases. Lysosomal storage diseases generally result from accumulation and/or failure to properly process certain cellular materials. The absence of a normally-occurring enzyme is typically the cause of disease. Currently, approximately 50 such diseases are known in humans and animals.

Gaucher's disease, a recessive disease, is representative. In Gaucher's disease, the lipid glucosylceramide accumulates in macrophages due to a lack of the enzyme glucocerebrosidase. Administration of the present delivery device comprising the gene for glucocerebrosidase or an equivalent thereof to an affected individual is expected to reduce the accumulation of glucosylceramide, thereby obviating the recessive defect and ameliorating the disease.

A particularly preferred delivery device for this indication is a species of Leishmania expressing glucocerebrosidase enzyme, Ceredase®, Cerezyme®, or equivalents and/or variants of the foregoing, because Leishmania can reside in the macrophages of a diseased individual, the actual site of the primary disease-producing event. It is not required, however, that the present device reside in macrophages; it is known that lysosomal enzymes can be transferred by endocytosis or by cell-to-cell transfer (see 1996 *Goodman & Gilman's The Pharmaceutical Basis of Therapeutics*, pp. 1487–1518; eds. J. G. Hardman, L. E. Limbird, P. B. Molinoff, R. W. Ruddon, & A. Goodman Gilman, 9th ed., McGraw-Hill, N.Y.). Additionally, it is anticipated that the present device can express glucocerebrosdiase enzyme, Ceredase®, Cerezyme®, or equivalents and/or variants of the foregoing, such that it is secreted. Alternatively, it can be associated with the device, for example the outer surface of the device to name but one alternative. All that is required is that the device provide enzyme to the diseased individual.

The skilled artisan will appreciate that other lysosomal storage diseases can be similarly treated. Furthermore, the skilled artisan will appreciate that the present invention can be used to accomplish enzyme replacement therapy in its broadest meaning.

Neural Disorders

It is anticipated that the present invention will permit treatment and/or amelioration of neural disorders. One particularly preferred neural disorder is Parkinson's Disease (PD). The primary defect in PD is loss of neurons in the substantia nigra pars compacta which provide dopaminergic innervation to the caudate and putamen striatum. It is well-known that replacement of dopamine can restore function and ameliorate clinical manifestations of PD, such as tremor and muscular rigidity.

The present invention comprises a delivery device which provides the host with substances such as levodopa (L-DOPA, LARODOPA, DOPAR, L-3,4-dihydroxyphenylanine), the metabolic precursor of dopamine. Levodopa is rapidly absorbed from the small bowel, thus the preferred device will reside in bowel and/or related organs to facilitate delivery. This is not required, however, since levodopa is currently administered orally indicating that any systemic route of delivery will be suitable. Alternatively, the preferred delivery device will reside in the brain, most preferably the substantia nigra. *T. cruzi* is an example of one preferred organism suitable for use as such a device in brain tissue. In another preferred embodiment, the present device will comprise the genetic machinery necessary to produce dopamine receptor agonists such as, but not limited to, bromocriptine and pergolide, including analogs and equivalents thereof.

The skilled artisan will appreciate that other neural disorders can be treated and/or ameliorated similarly with the present invention.

Hormonal Disorders

It is expected that the present invention will provide a sustained delivery device and method of treatment for hormonal disorders generally, more specifically for diseases related to insulin deficiencies or resistance. Currently preferred diseases include insulin-dependent diabetes mellitus (IDDM or type I), non-insulin-dependent diabetes mellitus (NIDDM or type II), and gestational diabetes mellitus, to name but a few. (See 1996 *Goodman & Gilman's The Pharmacological Basis of Therapeutics*, pp. 1487–1518; eds. J. G. Hardman, L. E. Limbird, P. B. Molinoff, R. W. Ruddon, & A. Goodman Gilman, 9th ed., McGraw-Hill, N.Y.).

At present, insulin supplementation is the treatment of virtually all IDDM and most NIDDM individuals. Supplementation is routinely accomplished by subcutaneous injection; dosages and repeated injections vary depending upon the particular individual. It is expected that all preparations of insulin can be delivered as disclosed herein. Such preparations are contemplated to include short-, intermediate-, and long-lasting forms from human, porcine, and bovine sources, as well as admixtures thereof. Particularly preferred is human insulin, most preferably recombinant human insulin. It is also anticipated that insulin analogs can be delivered as disclosed herein. For example, nonnative monomeric, dimeric, etc., forms with improved absorption properties can be delivered with the sustained delivery devices and methods disclosed herein. One particularly useful analog is a sequence-modified insulin in which naturally-occurring residues B28 and B29 in human insulin have been reversed. The skilled artisan will recognize that equivalents are within the scope of the instant invention. Equivalents can be identified using only routine experimentation. Additionally, in certain applications, human proinsulin can be delivered with the present invention.

With respect to routes of delivery, insulin can be administered orally, nasally, rectally and by subcutaneous means such as injections or implantation. The objective is to identify a route which provides higher relative concentrations of insulin in the portal circulation. Again, the present device is particularly useful because it can be designed to reside in a particular tissue, especially one which would most effectively deliver insulin to the portal circulation. A currently preferred tissue is skin. As explained earlier, Leishmania spp., particularly less virulent variants, can reside in the skin of the host, thereby permitting the skilled practitioner to target the present device to skin, if desired.

As earlier discussed, the present delivery device can be designed to express a preferred form of insulin. It is anticipated that the present device can be designed also to express other components involved in the regulation of insulin secretion. By way of example, it is anticipated that an insulin-delivering device will also comprise genetic information to permit entry of glucose into the device as would normally occur in the a cell of the islet of Langerhans. A device expressing the glucose reception as well as insulin can provide controlled insulin expression by autoregulation.

The skilled artisan will further appreciate that multiple devices can be designed, to mimic the functions of all the requisite cell types in the islet of Langerhans (β-cell, α-cell, δ-cell and PP or F cell; see the above-referenced 1996 *Goodman & Gilman's The Pharmacological Basis of Therapeutics*). These different devices can then be administered collectively, thereby providing the recipient with the equivalent of a functional islet of Langerhans. The skilled artisan will appreciate that the insulin therapy disclosed herein is only illustrative of the present invention's general applicability to ligand-receptor, hormone-mediated indications.

As stated above, the present invention contemplates that regulation of expression product can be accomplished by the organism per se. For example, a conditionally defective organism expressing a gene of interest can be further genetically modified so as to autoregulate expression of said gene; autoregulation can be achieved by exploiting receptor-ligand interactions, pH, temperature, salt concentration, enzyme-substrate dynamics, and genetic control mechanisms of the organism, to name but a few mechanisms underlying physiologically-relevant autoregulation. The insulin-glucose receptor interaction is exemplary of an autoregulating phenomenon within the scope of the present invention.

EXAMPLE 10

General Formulation/Administration Considerations

The delivery vehicles of the present invention can be administered to a mammalian host by any route. Thus, as appropriate, administration can be oral or parenteral, including intravenous and intraperitoneal routes of administration. In addition, administration can be by periodic injections of a bolus of the device, or can be made more continuous by intravenous or intraperitoneal administration from a reservoir which is external (e.g., an i.v. bag). In certain embodiments, the devices of the instant invention can be therapeutic-grade. That is, certain embodiments comply with standards of purity and quality control required for administration to humans. Veterinary applications are also within the intended meaning as used herein.

Useful solutions for oral or parenteral administration can be prepared by any of the methods well known in the pharmaceutical art, described, for example, in *Remington's Pharmaceutical Sciences*, (Gennaro, A., ed.), Mack Pub., 1990. administration, methoxysalicylate for rectal administration, or cutric acid for vaginal administration. Suppositories for rectal administration also can be prepared by mixing the device with a non-irritating excipient such as cocoa butter or other compositions which are solid at room temperature and liquid at body temperatures. Formulations can also include, for example, polyalkylene glycols such as polyethylene glycol, oils of vegetable origin, hydrogenated naphthalenes, and the like. Formulations for direct administration, in particular, can include glycerol and other compositions of high viscosity. Other potentially useful parenteral carriers for these devices include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally.

The formulations, both for veterinary and for human medical use, of the present invention comprise a sustained delivery device in association with a pharmaceutically acceptable carrier therefore and optionally other therapeutic ingredient(s). The carrier(s) must be "acceptable" in the sense of being compatible with the other ingredients of the formulations and not deleterious to the recipient thereof. The formulations may conveniently be presented in dosage unit form and may be prepared by any of the methods well known in the art of pharmacy/microbiology. All methods include the step of bringing the organism into association with the carrier which constitutes one or more accessory ingredients. In general, the formulations are prepared by bringing the organism into association with a liquid carrier or a finely divided solid carrier or both, and then, if necessary, shaping the product into the desire formulation.

Formulations of the present invention suitable for oral administration may be in the form of discrete units as capsules, sachets, tablets or lozenges, each containing a predetermined amount of the device; in the form of a powder or granules; in the form of a solution or a suspension in an aqueous liquid or non-aqueous liquid; or in the form of an oil-in-water emulsion or a water-in-oil emulsion. The device may also be administered in the form of a bolus, electuary or paste. A tablet may be made by compressing or moulding the device optionally with one or more accessory ingredients. Compressed tablets may be prepared by compressing, in a suitable machine, the device in a free-flowing form such as a powder or granules, optionally mixed by a binder, lubricant, inert diluent, surface active or dispersing agent. Moulded tablets may be made by moulding, in a suitable machine, a mixture of the powdered device and suitable carrier moistened with an inert liquid diluent.

Formulations suitable for intra-articular administration may be in the form of a sterile aqueous preparation of the device which may be in microcrystalline form, for example, in the form of an aqueous microcrystalline suspension. Liposomal formulations or biodegradable polymer systems may also be used to present the device for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pasts; or solutions or suspensions such as drops. Formulations for topical administration to the skin surface can be prepared by dispersing the device with a dermatologically acceptable carrier such as a lotion, cream, ointment or soap. Particularly useful are carriers capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

For asthma treatment, inhalation of powder (self-propelling or spray formulations) dispensed with a spray can, a nebulizer or an atomizer can be used. Such formulations are most preferably in the form of a finely comminuted powder for pulmonary administration from a powder inhalation device or self-propelling powder-dispensing formulations. In the case of self-propelling solution and spray formulations, the effect may be achieved either by choice of a valve having the desired spray characteristics (i.e., being capable of producing a spray having the desired particle size) or by incorporating the active ingredient as a suspended powder in controlled particle size.

Finally, the devices of the present invention can be administered alone or in combination with other molecules known to have a beneficial effect on the particular disease or indication of interest. By way of example only, useful cofactors include symptom-alleviating cofactors, including antiseptics, antibiotics, antiviral and antifungal agents and analgesics and anesthetics.

The present devices further can be formulated into pharmaceutical compositions by admixture with pharmaceutically acceptable nontoxic excipients and carriers. As noted above, such compositions can be prepared for parenteral administration, particularly in the form of liquid solutions or suspensions; for oral administration, particularly in the form of tablets or capsules; or intranasally, particularly in the form of powders, nasal drops or aerosols. Where adhesion to a tissue surface is desired the composition can include the device dispersed in a fibrinogen-thrombin composition or other bioadhesive. The device then can be painted, sprayed or otherwise applied to the desired tissue surface. Alternatively, the devices can be formulated for parenteral or oral administration to humans or other mammals, for example, in therapeutically effective amounts, e.g., amounts which provide appropriate concentrations of the device to target tissue for a time sufficient to induce the desired effect.

Where the device is to be used as part of a transplant procedure, it can be provided to the living tissue or organ to be transplanted prior to removal of tissue or organ from the donor. The device can be provided to the donor host.

Alternatively or, in addition, once removed from the donor, the organ or living tissue can be placed in a preservation solution containing the device. In all cases, the device can be administered directly to the desired tissue, as by injection to the tissue, or it can be provided systemically, either by oral or parenteral administration, using any of the methods and formulations described herein and/or known in the art.

Where the device comprises part of a tissue or organ preservation solution, any commercially available preservation solution can be used to advantage. For example, useful solutions known in the art include Collins solution, Wisconsin solution, Belzer solution, Eurocollins solution and lactated Ringer's solution. Generally, an organ preservation solution usually possesses one or more of the following properties: (a) an osmotic pressure substantially equal to that of the inside of a mammalian cell (solutions typically are hyperosmolar and have K+ and/or Mg++ ions present in an amount sufficient to produce an osmotic pressure slightly higher than the inside of a mammalian cell); (b) the solution typically is capable of maintaining substantially normal ATP levels in the cells; and (c) the solution usually allows optimum maintenance of glucose metabolism in the cells. Organ preservation solutions also can contain anticoagulants, energy sources such as glucose, fructose and other sugars, metabolites, heavy metal chelators, glycerol and other materials of high viscosity to enhance survival at low temperatures, free oxygen radical inhibiting and/or scavenging agents and a pH indicator. A detailed description of preservation solutions and useful components can be found, for example, in U.S. Pat. No. 5,002,965, the disclosure of which is incorporated herein by reference.

The number of organisms and/or the effective concentration of the compounds to be delivered in a therapeutic composition will vary depending upon a number of factors, including the final desired dosage of the compound to be administered, and the route of administration. The preferred dosage to be administered also is likely to depend on such variables as the type and extent of disease or indication to be treated, the overall health status of the particular patient, the relative biological efficacy of the compound delivered, the formulation of the device, the presence and types of excipients in the formulation, and the route of administration. In general terms, the devices of this invention can be provided to an individual using typical dose units deduced from the earlier-described mammalian studies using non-human primates and rodents. By the term dosage unit is meant a unitary, i.e. a single dose which is capable of being administered to a patient, and which may be readily handled and packed, remaining as a physically and biologically stable unit dose comprising either the device as such or a mixture of it with solid or liquid pharmaceutical diluents or carriers.

Finally, in another series of embodiments, cells can be utilized to serve as a carrier of the sustained delivery devices disclosed herein.

Where the device is intended for use as a therapeutic to alleviate disease associated with the central nervous system (CNS) an additional administration problem may need to be addressed: overcoming the so-called "blood-brain barrier", the brain capillary wall structure that effectively screens out all but selected categories of molecules present in the blood, preventing their passage into the brain. The blood-brain barrier may be bypassed effectively by direct infusion of the device into the brain. In certain preferred embodiments, however, the blood-barrier can be circumvented by using a device comprising an organism with an inherent ability to penetrate the blood-brain barrier, i.e., an organism with tissue-specificity for the brain such as, for example, *T. cruzi*. Alternatively, the device can be further genetically-modified to insure that the desired expression product is modified to enhance its transport across the blood-brain barrier. For example, truncated forms of the expression product may be most successful. Alternatively, the expression product may be modified to render it more lipophilic, or it may be conjugated to another molecule which is naturally transported across the barrier, using standard means known to those skilled in the art, as, for example, described in Pardridge, *Endocrine Reviews*: 7:314–330 (1986) and U.S. Pat. No. 4,801,575.

When a sustained delivery device for the instant invention is intended for administration to a plant host, the invention may be applied directly to the plant environment, for example, to the surface of leaves, buds, roots or floral parts. Alternatively, the present invention can be used as a seed coating. The determination of an effective amount of the present invention as required for a particular plant is within the skill of the art and will depend on such factors as the plant species, method of planting, and soil type. Generally speaking, it is anticipated that application of approximately $10^3$–$10^{10}$ organisms per seed will be sufficient to ensure proper exposure. Typically, 0.1–200 nanograms of expression product per organism will provide adequate exposure, however, precise dosages will vary with the organism, host and indication of interest. Determination of such specifics requires only routine skill. It is contemplated that compositions containing the device of the invention can be prepared by formulating the organism device with adjuvants, diluents, carriers, etc., to provide compositions in the form of filings/divided particulate solids, granules, pellets, wetable powders, dust, aquerus suspensions or dispersions, and emulsions. It is further contemplated to use the device in capsulated form, for example, the device can be encapsulated within polymer, gelatin, liptids or other formulation aids such as emulsifiers, surfactants wetting agents, antifoam agents and anti-freeze agents, may be incorporated into such compositions especially if such compositions will be stored for any period of time prior to use. Application of compositions containing the delivery devices of the invention as the active agent can be carried out by conventional techniques.

When a sustained delivery device is intended for administration to an insect host, standard methods such as, but not limited to, aerial dispersal are contemplated.

EQUIVALENTS

The invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims rather than by the foregoing description, and all changes which come within the meaning and range of equivalency of the claims are therefore intended to be embraced therein.

What is claimed is:

1. A method for producing an expression product in Leishmania, the method comprising the steps of:

transfecting a Leishmania organism with a nucleic acid comprising a nucleotide sequence encoding an expression product and a nucleotide sequence complementary to a wild type nucleotide sequence flanking a genetic locus in the genome of said organism; and, selecting for a conditionally defective phenotype generated by loss of said genetic locus from said genome, wherein the introduction of said nucleic acid into said organism results in the production of said expression product.

2. A method for producing an expression product from a Leishmania organism, the method comprising the steps of:

providing a conditionally defective Leishmania organism that expresses an expression product, wherein said conditionally defective organism was produced by selecting for a conditionally defective phenotype generated by loss of a genetic locus from the genome of a Leishmania organism transfected with a nucleic acid comprising a nucleotide sequence encoding said expression product and a nucleotide sequence complementary to a wild type nucleotide sequence flanking said genetic locus; and, growing said conditionally defective organism to produce said expression product.

3. The method of claim 2, wherein said growing step comprises culturing said conditionally defective organism in vitro.

4. The method of claim 2, wherein said expression product is a hormone, enzyme, or neurotransmitter.

5. The method of claim 2, wherein said expression product is used to treat a lysosomal storage disease.

6. The method of claim 2 wherein said expression product is glucocerebrosidase.

* * * * *